United States Patent
Verdin et al.

(10) Patent No.: US 9,474,788 B2
(45) Date of Patent: Oct. 25, 2016

(54) METHODS FOR THE REACTIVATION OF LATENT HIV USING CYTOSINE METHYLATION INHIBITORS AND NF-KB ACTIVATORS

(75) Inventors: Eric M. Verdin, San Francisco, CA (US); Steven E. Kauder, San Francisco, CA (US)

(73) Assignee: The J. David Gladstone Institutes, San Francisco, CA (US)

( * ) Notice: Subject to any disclaimer, the term of this patent is extended or adjusted under 35 U.S.C. 154(b) by 586 days.

(21) Appl. No.: 13/088,136

(22) Filed: Apr. 15, 2011

(65) Prior Publication Data
US 2011/0305662 A1   Dec. 15, 2011

Related U.S. Application Data

(60) Provisional application No. 61/333,135, filed on May 10, 2010.

(51) Int. Cl.
| | | |
|---|---|---|
| *A61K 38/19* | (2006.01) | |
| *A61K 31/15* | (2006.01) | |
| *A61K 31/166* | (2006.01) | |
| *A61K 31/353* | (2006.01) | |
| *A61K 31/405* | (2006.01) | |
| *A61K 31/495* | (2006.01) | |
| *A61K 31/513* | (2006.01) | |
| *A61K 31/7068* | (2006.01) | |
| *A61K 38/17* | (2006.01) | |
| *A61K 38/20* | (2006.01) | |
| *A61K 45/06* | (2006.01) | |

(52) U.S. Cl.
CPC ............ *A61K 38/191* (2013.01); *A61K 31/15* (2013.01); *A61K 31/166* (2013.01); *A61K 31/353* (2013.01); *A61K 31/405* (2013.01); *A61K 31/495* (2013.01); *A61K 31/513* (2013.01); *A61K 31/7068* (2013.01); *A61K 38/1709* (2013.01); *A61K 38/2006* (2013.01); *A61K 45/06* (2013.01); *C12N 2740/16011* (2013.01)

(58) Field of Classification Search
CPC ............ A61K 38/191; A61K 31/495; C12N 2740/16011
See application file for complete search history.

(56) References Cited

U.S. PATENT DOCUMENTS

| 7,232,685 B2 | 6/2007 | Verdin et al. |
| 7,544,467 B2 | 6/2009 | Verdin et al. |
| 2009/0305227 A1 | 12/2009 | Dougherty et al. |

OTHER PUBLICATIONS

Tremblay, C., 2004, Effects of HIV-1 Entry Inhibitors in Combination, Curr. Pharm. Des. 10:1861-1865.*
Chou, T.-C., 2010, Drug Combination Studies and Their Synergy Quantification Using the Chou-Talalay Method, Cancer Res. 70(2):440-446.*
Blazkova, J., et al., Aug. 2009, CpG Methylation Controls Reactivation of HIV from Latency, PLoS Pathogens 5(8):e1000554 (1-14).*
Gait, M. J., and J. Karn, Oct. 1995, Progress in anti-HIV structure-based drug design, TIBTECH 13:430-438.*
Geeraert et al.: "Hide-and-seek: The Challenge of Viral Persistence in HIV-1 Infection", Annual Review of Medicine, 2008, pp. 487-501, vol. 59.
Kauder et al.: "Epigenetic Regulation of HIV-1 Latency by Cytosine Methylation", PLOS Pathogens, Jun. 2009, pp. 1-15, vol. 5, No. 6.
Pierson et al.: "Reservoirs for HIV-1: Mechanisms for Viral Persistence in the Presence of Antiviral Immune Responses and Antiretroviral Therapy", Annual Review of Immunology, 2000, pp. 665-708, vol. 18.

* cited by examiner

*Primary Examiner* — Jeffrey Parkin
(74) *Attorney, Agent, or Firm* — Michael B. Rubin; Bozicevic, Field & Francis LLP

(57) ABSTRACT

The present disclosure provides methods and compositions for reactivating latent immunodeficiency virus in an immunodeficiency virus-infected cell. The methods generally involve contacting an immunodeficiency virus-infected cell with a synergistically effective amount of an inhibitor of cytosine methylation and an NF-κB activator. The present disclosure provides methods and compositions for reducing the reservoir of latent immunodeficiency virus in an individual, and for treating an immunodeficiency virus infection in an individual.

7 Claims, 10 Drawing Sheets

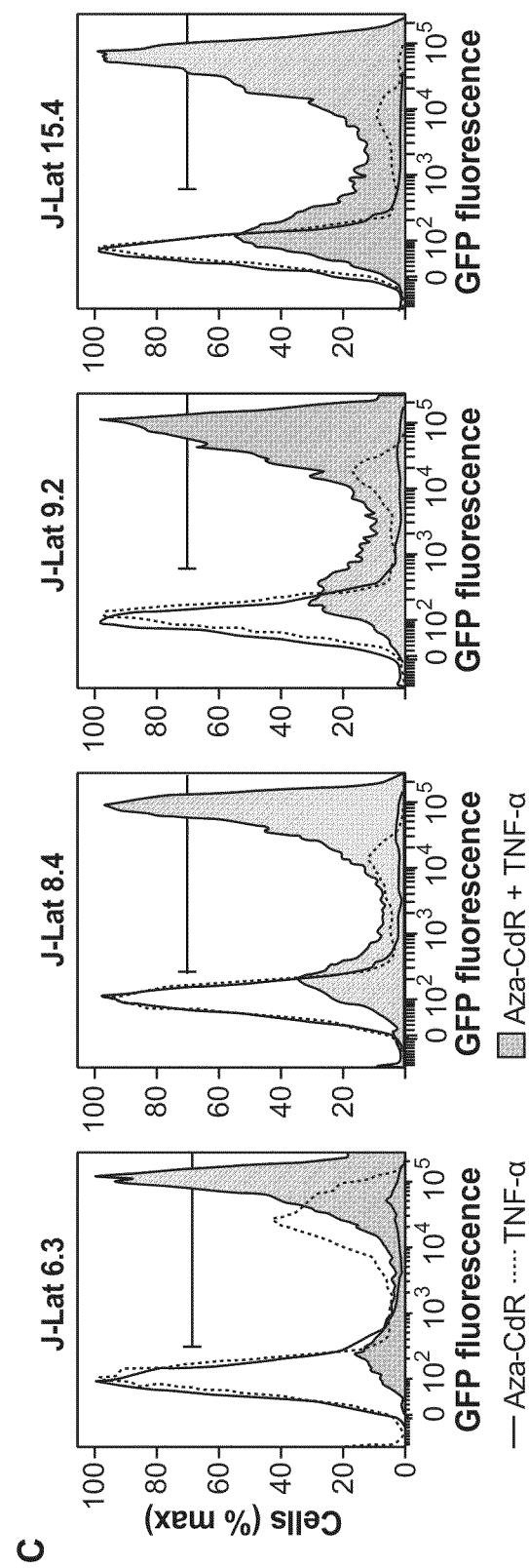
FIG. 4 (Cont.1)

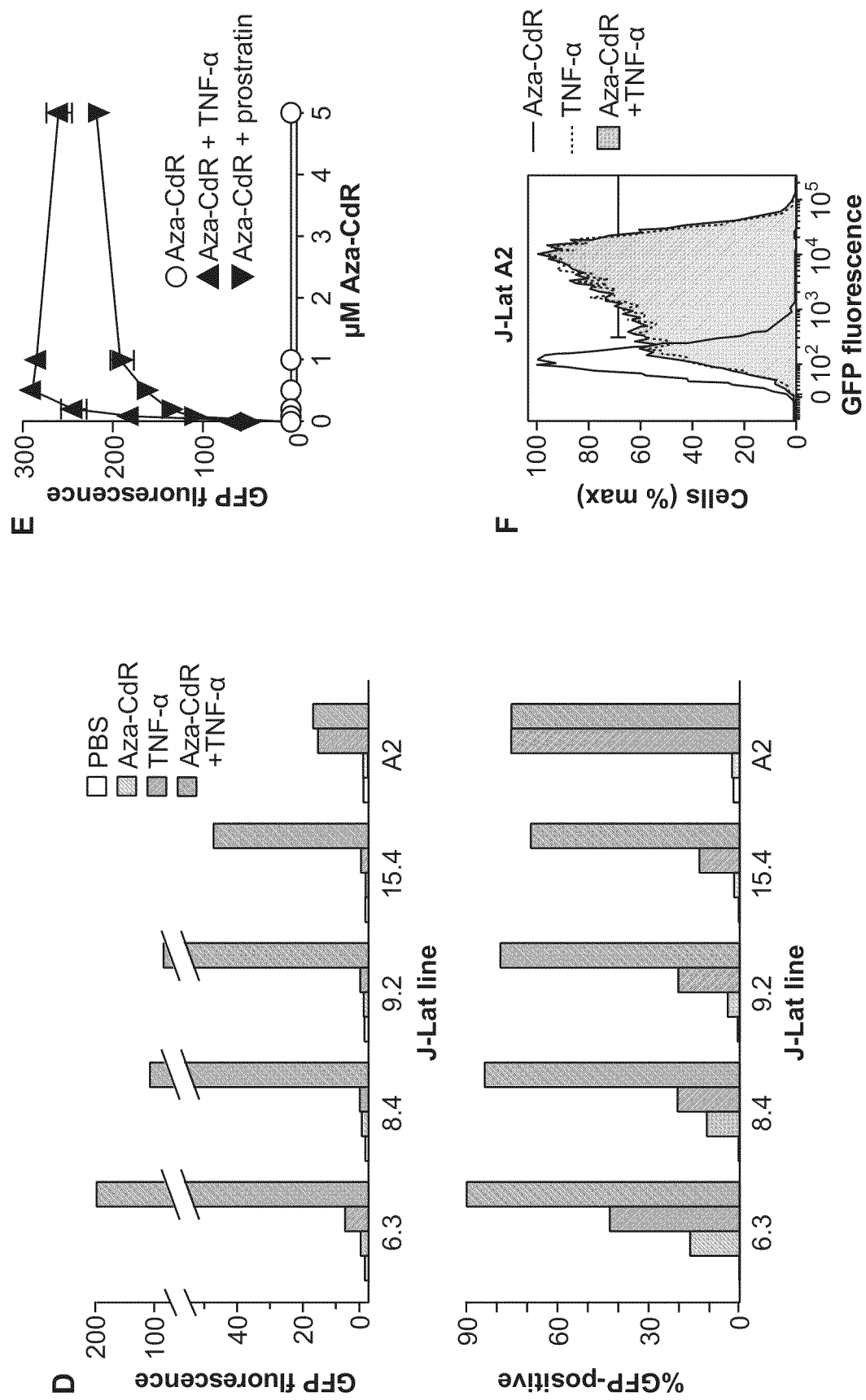
FIG. 4 (Cont.2)

```
        U3
-454  TGGAAGGGCTAATTCACTCCCAACGAAGACAAGATATCCTTGATCTGTGGA  -404
-403  TCTACCACACACAAGGCTACTTCCCTGATTAGCAGAACTACACACCAGGGC  -353
-352  CAGGGATCAGATATCCACTGACCTTTGGATGGTGCTACAAGCTAGTACCAG  -302
-301  TTGAGCCAGAGAAGTTAGAAGAAGCCAACAAAGGAGAGAACACCAGCTTGT  -251
-250  TACACCCTGTGAGCCTGCATGGAATGGATGACCCGGAGAGAGAAGTGTTAG  -200
-199  AGTGGAGCTTTGACAGCCGCCTAGCATTTCATCACATGGCCCGAGAGCTGC  -149
-148  ATCCGGAGTACTTCAAGAACTGCTGACATCGAGCTTGCTACAAGGGACTTT   -98
 -97  CCGCTGGGGACTTTCCAGGGAGGCGTGGCCTGGGCGGGACTGGGGAGTGCC   -47
                                                     R
 -46  GAGCCCTCAGATCCTGCATATAAGCAGCTGCTTTTTGCCTGTACTGGGTCT    4
   5  CTCTGGTTAGACCAGATCTGAGCCTGGGAGCTCTCTGGCTAACTAGGGAAC   55
                                                    U5
  56  CCACTGCTTAAGCCTCAATAAAGCTTGCCTTGAGTGCTTCAAGTAGTGTGT  106
 107  GCCCGTCTGTTGTGTGACTCTGGTAACTAGAGATCCCTCAGACCCTTTTAG  157
 158  TCAGTGTGGAAAATCTCTAGCAGTGGCGCCCGAACAGGGACCTGAAACGA   208
 209  AAGGGAAACCAGAGGAGCTCTCTCGACGCAGGACTCGGCTTGCTGAAGCGC  259
 260  GCACGGCAAGAGGCGAGGGGCGGCGACTGGTGAGTACGCCAAAAATTTTGA  310
                                       Gag
 311  CTAGCGGAGGCTAGAAGGAGAGAGATGGGTGCGAGAGCGTCAGTATTAAGC  361
 362  GGGGAGAATTAGATCGATGGGAAAAAATTCGGTTAAGGCCAGGGGGAAAG   412
 413  AAAAAATATAAATTAAAACATATAGTATGGGCAAGCAGGGAGCTAGAACGA  463
 464  TTCGCAGTTAATCCTGGCCTGTTAGAAACATCAGAAGGCTGTAGACAAATA  514
 515  CTGGGACAGCTACAACCATCCCTTCAGACAG                      546
```

FIG. 7

SEQUENCE LISTING

<160> NUMBER OF SEQ ID NOS: 27

<210> SEQ ID NO 1
<211> LENGTH: 233
<212> TYPE: PRT
<213> ORGANISM: Homo sapiens

<400> SEQUENCE: 1

Met Ser Thr Glu Ser Met Ile Arg Asp Val Glu Leu Ala Glu Glu Ala
1               5                   10                  15

Leu Pro Lys Lys Thr Gly Gly Pro Gln Gly Ser Arg Arg Cys Leu Phe
            20                  25                  30

Leu Ser Leu Phe Ser Phe Leu Ile Val Ala Gly Ala Thr Thr Leu Phe
        35                  40                  45

Cys Leu Leu His Phe Gly Val Ile Gly Pro Gln Arg Glu Glu Phe Pro
    50                  55                  60

Arg Asp Leu Ser Leu Ile Ser Pro Leu Ala Gln Ala Val Arg Ser Ser
65                  70                  75                  80

Ser Arg Thr Pro Ser Asp Lys Pro Val Ala His Val Val Ala Asn Pro
                85                  90                  95

Gln Ala Glu Gly Gln Leu Gln Trp Leu Asn Arg Arg Ala Asn Ala Leu
            100                 105                 110

Leu Ala Asn Gly Val Glu Leu Arg Asp Asn Gln Leu Val Val Pro Ser
        115                 120                 125

Glu Gly Leu Tyr Leu Ile Tyr Ser Gln Val Leu Phe Lys Gly Gln Gly
    130                 135                 140

Cys Pro Ser Thr His Val Leu Leu Thr His Thr Ile Ser Arg Ile Ala
145                 150                 155                 160

Val Ser Tyr Gln Thr Lys Val Asn Leu Leu Ser Ala Ile Lys Ser Pro
                165                 170                 175

Cys Gln Arg Glu Thr Pro Glu Gly Ala Glu Ala Lys Pro Trp Tyr Glu
            180                 185                 190

Pro Ile Tyr Leu Gly Gly Val Phe Gln Leu Glu Lys Gly Asp Arg Leu
        195                 200                 205

Ser Ala Glu Ile Asn Arg Pro Asp Tyr Leu Asp Phe Ala Glu Ser Gly
    210                 215                 220

Gln Val Tyr Phe Gly Ile Ile Ala Leu
225                 230

<210> SEQ ID NO 2
<211> LENGTH: 1000
<212> TYPE: DNA
<213> ORGANISM: Lentivirus retroviridae

<400> SEQUENCE: 2
tggaagggct aattcactcc caacgaagac aagatatcct tgatctgtgg atctaccaca      60
cacaaggcta cttccctgat tagcagaact acacaccagg gccagggatc agatatccac     120
tgacctttgg atggtgctac aagctagtac cagttgagcc agagaagtta gaagaagcca     180
acaaggagag gaacaccagc ttgttacacc ctgtgagcct gcatggaatg gatgacccgg     240
agagagaagt gttagagtgg aggtttgaca gccgcctagc atttcatcac atggcccgag     300
agctgcatcc ggagtacttc aagaactgct gacatcgagc ttgctacaag ggactttccg     360
ctggggactt tccagggagg cgtggcctgg gcgggactgg ggagtggcga gccctcagat     420
cctgcatata agcagctgct ttttgcctgt actgggtctc tctggttaga ccagatctga     480
gcctgggagc tctctggcta actagggaac ccactgctta agcctcaata agcttgcct      540 tgagtgcttc aagtagtgtg tgcccgtctg ttgtgtgact ctggtaacta gagatccctc     600
agaccctttt agtcagtgtg gaaaatctct agcagtggcg cccgaacagg gacctgaaag     660
cgaaagggaa accagaggag ctctctcgac gcaggactcg gcttgctgaa gcgcgcacgg     720
caagaggcga gggcggcga ctggtgagta cgccaaaaat tttgactagc ggaggctaga     780
aggagagaga tgggtgcgag agcgtcagta ttaagcgggg gagaattaga tcgatgggaa     840
aaaattcggt taaggccagg gggaaagaaa aaatataaat taaaacatat agtatgggca     900
agcagggagc tagaacgatt cgcagttaat cctggcctgt tagaaacatc agaaggctgt     960
agacaaatac tgggacagct acaaccatcc cttcagacag                          1000

<210> SEQ ID NO 3
<211> LENGTH: 36
<212> TYPE: PRT
<213> ORGANISM: Artificial Sequence
<220> FEATURE:
<223> OTHER INFORMATION: Synthetic polypeptide
<220> FEATURE:
<221> NAME/KEY: ACETYLATION
<222> LOCATION: 1
<223> OTHER INFORMATION: N-terminal acetylation
<220> FEATURE:
<221> NAME/KEY: AMIDATION
<222> LOCATION: 36
<223> OTHER INFORMATION: C-terminal amide

<400> SEQUENCE: 3

Tyr Thr Ser Leu Ile His Ser Leu Ile Glu Glu Ser Gln Asn Gln Gln
1               5                   10                  15

Glu Lys Asn Glu Gln Glu Leu Leu Glu Leu Asp Lys Trp Ala Ser Leu

```
                20                  25                  30
Trp Asn Trp Phe
        35

<210> SEQ ID NO 4
<211> LENGTH: 25
<212> TYPE: DNA
<213> ORGANISM: Artificial Sequence
<220> FEATURE:
<223> OTHER INFORMATION: Synthetic primer

<400> SEQUENCE: 4
aaatgggcgg taggcgtgta cggtg                                  25

<210> SEQ ID NO 5
<211> LENGTH: 25
<212> TYPE: DNA
<213> ORGANISM: Artificial Sequence
<220> FEATURE:
<223> OTHER INFORMATION: Synthetic primer

<400> SEQUENCE: 5
gcggcttcgg ccagtaacgt taggg                                  25

<210> SEQ ID NO 6
<211> LENGTH: 21
<212> TYPE: DNA
<213> ORGANISM: Artificial Sequence
<220> FEATURE:
<223> OTHER INFORMATION: Synthetic primer

<400> SEQUENCE: 6
atggtgagca agggcgagga g                                      21

<210> SEQ ID NO 7
<211> LENGTH: 20
<212> TYPE: DNA
<213> ORGANISM: Artificial Sequence
<220> FEATURE:
<223> OTHER INFORMATION: Synthetic primer

<400> SEQUENCE: 7
gtggtgcaga tgaacttcag                                        20

<210> SEQ ID NO 8
<211> LENGTH: 18
<212> TYPE: DNA
<213> ORGANISM: Artificial Sequence
<220> FEATURE:
<223> OTHER INFORMATION: Synthetic primer

<400> SEQUENCE: 8
gccagctgca agccttgg                                          18

<210> SEQ ID NO 9
<211> LENGTH: 18
<212> TYPE: DNA
<213> ORGANISM: Artificial Sequence
<220> FEATURE:
<223> OTHER INFORMATION: Synthetic primer

<400> SEQUENCE: 9
gccactgggc ctccattc                                          18

<210> SEQ ID NO 10
```

```
<211> LENGTH: 23
<212> TYPE: DNA
<213> ORGANISM: Artificial Sequence
<220> FEATURE:
<223> OTHER INFORMATION: Synthetic primer

<400> SEQUENCE: 10
cccacaacga atgaatgaac agc                                              23

<210> SEQ ID NO 11
<211> LENGTH: 22
<212> TYPE: DNA
<213> ORGANISM: Artificial Sequence
<220> FEATURE:
<223> OTHER INFORMATION: Synthetic primer

<400> SEQUENCE: 11
tgaagacctt tgggtagttc ca                                               22

<210> SEQ ID NO 12
<211> LENGTH: 20
<212> TYPE: DNA
<213> ORGANISM: Artificial Sequence
<220> FEATURE:
<223> OTHER INFORMATION: Synthetic primer

<400> SEQUENCE: 12
gtctcctttg agctgtttgc                                                  20

<210> SEQ ID NO 13
<211> LENGTH: 20
<212> TYPE: DNA
<213> ORGANISM: Artificial Sequence
<220> FEATURE:
<223> OTHER INFORMATION: Synthetic primer

<400> SEQUENCE: 13
ccatagatgg acttgccacc                                                  20

<210> SEQ ID NO 14
<211> LENGTH: 23
<212> TYPE: DNA
<213> ORGANISM: Artificial Sequence
<220> FEATURE:
<223> OTHER INFORMATION: Synthetic primer

<400> SEQUENCE: 14
ctccgagact ttcgaggaaa tac                                              23

<210> SEQ ID NO 15
<211> LENGTH: 23
<212> TYPE: DNA
<213> ORGANISM: Artificial Sequence
<220> FEATURE:
<223> OTHER INFORMATION: Synthetic primer

<400> SEQUENCE: 15
gccattgtag ttggtagcct tca                                              23

<210> SEQ ID NO 16
<211> LENGTH: 34
<212> TYPE: DNA
<213> ORGANISM: Artificial Sequence
<220> FEATURE:
<223> OTHER INFORMATION: Synthetic primer

<400> SEQUENCE: 16
```
cgcctcgagt ttattgattt ttggatggtg ttat                                34

<210> SEQ ID NO 17
<211> LENGTH: 34
<212> TYPE: DNA
<213> ORGANISM: Artificial Sequence
<220> FEATURE:
<223> OTHER INFORMATION: Synthetic primer

<400> SEQUENCE: 17
cgctctagac catttacccc taaatattct acac                                34

<210> SEQ ID NO 18
<211> LENGTH: 34
<212> TYPE: DNA
<213> ORGANISM: Artificial Sequence
<220> FEATURE:
<223> OTHER INFORMATION: Synthetic primer

<400> SEQUENCE: 18
cgcctcgaga tattttgtga gtttgtatgg gatg                                34

<210> SEQ ID NO 19
<211> LENGTH: 27
<212> TYPE: DNA
<213> ORGANISM: Artificial Sequence
<220> FEATURE:
<223> OTHER INFORMATION: Synthetic primer

<400> SEQUENCE: 19
cgctctagac ccaatattta tctacaa                                        27

<210> SEQ ID NO 20
<211> LENGTH: 34
<212> TYPE: DNA
<213> ORGANISM: Artificial Sequence
<220> FEATURE:
<223> OTHER INFORMATION: Synthetic primer

<400> SEQUENCE: 20
cgcctcgagt ttattgattt ttggatggtg tttt                                34

<210> SEQ ID NO 21
<211> LENGTH: 34
<212> TYPE: DNA
<213> ORGANISM: Artificial Sequence
<220> FEATURE:
<223> OTHER INFORMATION: Synthetic primer

<400> SEQUENCE: 21
cgctctagac catttacccc taaaaattct acac                                34

<210> SEQ ID NO 22
<211> LENGTH: 34
<212> TYPE: DNA
<213> ORGANISM: Artificial Sequence
<220> FEATURE:
<223> OTHER INFORMATION: Synthetic primer

<400> SEQUENCE: 22
cgcctcgaga tattttatga gttagtatgg gatg                                34

<210> SEQ ID NO 23
<211> LENGTH: 25
<212> TYPE: DNA

<213> ORGANISM: Artificial Sequence
<220> FEATURE:
<223> OTHER INFORMATION: Synthetic primer

<400> SEQUENCE: 23
tcagttcaga taatttcagt tgtcc          25

<210> SEQ ID NO 24
<211> LENGTH: 20
<212> TYPE: DNA
<213> ORGANISM: Artificial Sequence
<220> FEATURE:
<223> OTHER INFORMATION: Synthetic primer

<400> SEQUENCE: 24
cccagtacag gcaaaaagca                20

<210> SEQ ID NO 25
<211> LENGTH: 20
<212> TYPE: DNA
<213> ORGANISM: Artificial Sequence
<220> FEATURE:
<223> OTHER INFORMATION: Synthetic primer

<400> SEQUENCE: 25
aagcgaaagg gaaaccagag                20

<210> SEQ ID NO 26
<211> LENGTH: 20
<212> TYPE: DNA
<213> ORGANISM: Artificial Sequence
<220> FEATURE:
<223> OTHER INFORMATION: Synthetic primer

<400> SEQUENCE: 26
tctcccccgc ttaatactga                20

<210> SEQ ID NO 27
<211> LENGTH: 425
<212> TYPE: PRT
<213> ORGANISM: Homo sapiens

<400> SEQUENCE: 27

Met Asp Lys Asn Ile Gly Glu Gln Leu Asn Lys Ala Tyr Glu Ala Phe
 1               5                  10                  15

Arg Gln Ala Cys Met Asp Arg Asp Ser Ala Val Lys Glu Leu Gln Gln
                20                  25                  30

Lys Thr Glu Asn Tyr Glu Gln Arg Ile Arg Glu Gln Glu Gln Glu Leu
            35                  40                  45

Ser Leu Gln Gln Thr Ile Ile Asp Lys Leu Lys Ser Gln Leu Leu Leu
        50                  55                  60

Val Asn Ser Thr Gln Asp Asn Asn Tyr Gly Cys Val Pro Leu Leu Glu
65                  70                  75                  80

Asp Ser Glu Thr Arg Lys Asn Asn Leu Thr Leu Asp Gln Pro Gln Asp
                85                  90                  95

Lys Val Ile Ser Gly Ile Ala Arg Glu Lys Leu Pro Lys Val Arg Arg
            100                 105                 110

Gln Glu Val Ser Ser Pro Arg Lys Glu Thr Ser Ala Arg Ser Leu Gly
        115                 120                 125

Ser Pro Leu Leu His Glu Arg Gly Asn Ile Glu Lys Thr Phe Trp Asp
    130                 135                 140

```
Leu Lys Glu Glu Phe His Lys Ile Cys Met Leu Ala Lys Ala Gln Lys
145                 150                 155                 160

Asp His Leu Ser Lys Leu Asn Ile Pro Asp Thr Ala Thr Glu Thr Gln
                165                 170                 175

Cys Ser Val Pro Ile Gln Cys Thr Asp Lys Thr Asp Lys Gln Glu Ala
            180                 185                 190

Leu Phe Lys Pro Gln Ala Lys Asp Asp Ile Asn Arg Gly Ala Pro Ser
        195                 200                 205

Ile Thr Ser Val Thr Pro Arg Gly Leu Cys Arg Asp Glu Glu Asp Thr
        210                 215                 220

Ser Phe Glu Ser Leu Ser Lys Phe Asn Val Lys Phe Pro Pro Met Asp
225                 230                 235                 240

Asn Asp Ser Thr Phe Leu His Ser Thr Pro Glu Arg Pro Gly Ile Leu
            245                 250                 255

Ser Pro Ala Thr Ser Glu Ala Val Cys Gln Glu Lys Phe Asn Met Glu
            260                 265                 270

Phe Arg Asp Asn Pro Gly Asn Phe Val Lys Thr Glu Glu Thr Leu Phe
            275                 280                 285

Glu Ile Gln Gly Ile Asp Pro Ile Ala Ser Ala Ile Gln Asn Leu Lys
290                 295                 300

Thr Thr Asp Lys Thr Lys Pro Ser Asn Leu Val Asn Thr Cys Ile Arg
305                 310                 315                 320

Thr Thr Leu Asp Arg Ala Ala Cys Leu Pro Pro Gly Asp His Asn Ala
                325                 330                 335

Leu Tyr Val Asn Ser Phe Pro Leu Leu Asp Pro Ser Asp Ala Pro Phe
            340                 345                 350

Pro Ser Leu Asp Ser Pro Gly Lys Ala Ile Arg Gly Pro Gln Gln Pro
            355                 360                 365

Ile Trp Lys Pro Phe Pro Asn Gln Asp Ser Asp Ser Val Val Leu Ser
            370                 375                 380

Gly Thr Asp Ser Glu Leu His Ile Pro Arg Val Cys Glu Phe Cys Gln
385                 390                 395                 400

Ala Val Phe Pro Pro Ser Ile Thr Ser Arg Gly Asp Phe Leu Arg His
                405                 410                 415

Leu Asn Ser His Phe Asn Gly Glu Thr
            420                 425
```

METHODS FOR THE REACTIVATION OF LATENT HIV USING CYTOSINE METHYLATION INHIBITORS AND NF-KB ACTIVATORS

CROSS-REFERENCE

This application claims the benefit of U.S. Provisional Patent Application No. 61/333,135, filed May 10, 2010, which application is incorporated herein by reference in its entirety.

STATEMENT REGARDING FEDERALLY SPONSORED RESEARCH

This invention was made with government support under Grant Nos. F32 AI068531 and P01 AI058708 awarded by the National Institutes of Health. The government has certain rights in the invention.

BACKGROUND

Combination antiretroviral therapy can control HIV-1 replication and delay disease progression. However, despite the complete suppression of detectable viremia in many patients, viremia reemerges rapidly after interruption of treatment, consistent with the existence of a latent viral reservoir. This reservoir is thought to consist mainly of latently infected resting memory $CD4^+$ T cells. Due to the long half-life of this reservoir (44 months), it has been estimated that its total eradication with current treatment would require over 60 years.

Latently infected cells contain replication-competent integrated HIV-1 genomes that are blocked at the transcriptional level, resulting in the absence of viral protein expression. HIV depends on both cellular and viral factors for efficient transcription of its genome, and the activity of the HIV promoter is tightly linked to the level of activation of its host cell.

LITERATURE

U.S. Patent Publication No. 2009/0305227; Kauder et al. (June, 2009) *PLoS Pathogens* 5:1; U.S. Pat. No. 7,232,685; U.S. Pat. No. 7,544,467; Geeraert et al. (2008) *Annu. Rev. Med.* 59:487; Pierson et al. (2000) *Annu. Rev. Immunol.* 18:665.

SUMMARY OF THE INVENTION

The present disclosure provides methods and compositions for reducing the reservoir of latent immunodeficiency virus in an individual, and for treating an immunodeficiency virus infection in an individual.

BRIEF DESCRIPTION OF THE DRAWINGS

FIG. 7 depicts the nucleotide sequence of the first 1000 bases of HIV-1 strain HXB2 provirus (SEQ ID NO:2). The locations of CpG islands 1 and 2 are indicated. The U5, R, and U3 regions of the HIV-1 promoter are indicated.

DEFINITIONS

Figure 1:
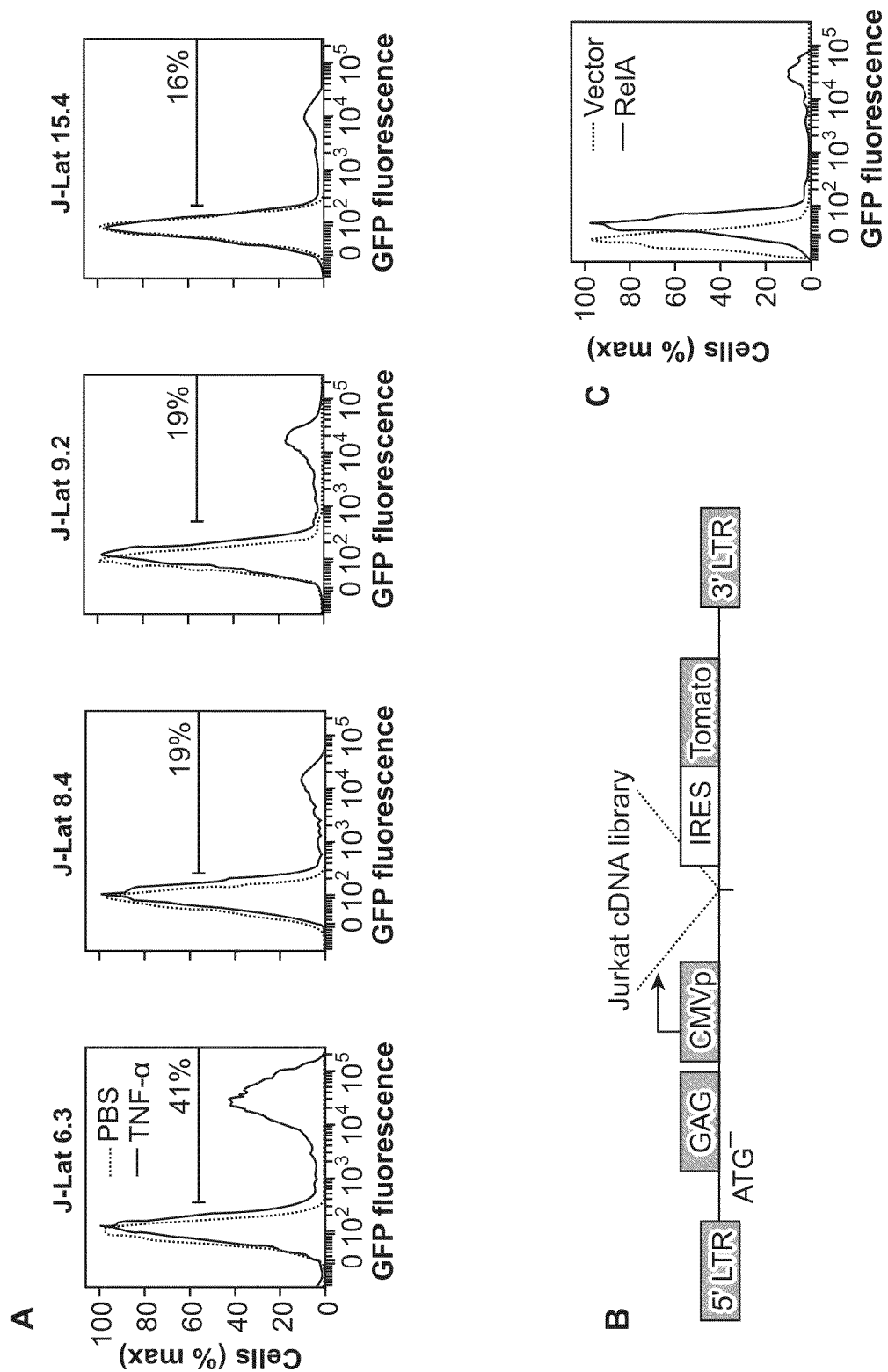
FIGS. 1A-C depict a cDNA screen to identify regulators of HIV-1 latency.

The term "immunodeficiency virus" includes human immunodeficiency virus (HIV), feline immunodeficiency virus, and simian immunodeficiency virus. The term "human immunodeficiency virus" as used herein, refers to human immunodeficiency virus-1 (HIV-1); human immunodeficiency virus-2 (HIV-2); and any of a variety of HIV subtypes and quasispecies.

As used herein, the terms "treat," "treatment," "treating," and the like, refer to obtaining a desired pharmacologic and/or physiologic effect. The effect may be prophylactic in terms of completely or partially preventing a disease or symptom thereof and/or may be therapeutic in terms of a partial or complete cure for a disease and/or adverse affect attributable to the disease. "Treatment," as used herein, covers any treatment of a disease in a mammal, particularly in a human, and includes: (a) preventing the disease from occurring in a subject which may be predisposed to the disease but has not yet been diagnosed as having it; (b) inhibiting the disease, i.e., arresting its development; and (c) relieving the disease, e.g., causing regression of the disease, e.g., to completely or partially remove symptoms of the disease. In the context of immunodeficiency virus infection, the term "treatment" encompasses prevention of establishment of a systemic infection following initial contact with the virus; and prophylactic treatment of an individual not yet infected with the virus.

The terms "co-administration" and "in combination with" include the administration of two or more therapeutic agents either simultaneously, concurrently or sequentially within no specific time limits. In one embodiment, the agents are present in the cell or in the subject's body at the same time or exert their biological or therapeutic effect at the same time. In one embodiment, the therapeutic agents are in the same composition or unit dosage form. In other embodiments, the therapeutic agents are in separate compositions or unit dosage forms. In certain embodiments, a first agent can be administered prior to (e.g., minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks before), concomitantly with, or subsequent to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks after) the administration of a second therapeutic agent.

As used herein, a "synergistic combination" or a "synergistic amount" of a cytosine methylation inhibitor and an NF-κB activator is a combined dosage that is more effective in reactivating a latent immunodeficiency virus than the incremental improvement in treatment outcome that could be predicted or expected from a merely additive combination of (i) the therapeutic or prophylactic benefit of the cytosine methylation inhibitor or the NF-κB activator when administered at that same dosage as a monotherapy.

Before the present invention is further described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a," "an," and "the" include plural referents unless the context clearly dictates otherwise. Thus, for example, reference to "an NF-κB activator" includes a plurality of such activators and reference to "the cytosine methylation inhibitor" includes reference to one or more cytosine methylation inhibitors and equivalents thereof known to those skilled in the art, and so forth. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

DETAILED DESCRIPTION

The present disclosure provides methods of treating an immunodeficiency virus infection in an individual; and methods of reducing the reservoir of latent immunodeficiency virus in an individual. The methods generally involve administering to an individual in need thereof a cytosine methylation inhibitor and an NF-κB activator in amounts effective to activate latent immunodeficiency virus. The combination of cytosine methylation inhibitor and an NF-κKB activator can be administered as part of a combination therapy with at least one anti-immunodeficiency virus therapeutic agent.

A cytosine methylation inhibitor and an NF-κB activator exhibit synergistic effects in reactivating latent immunodeficiency virus. Thus, the efficacy of the combination (e.g., combined administration, including where the two agents are administered together in a single composition, simultaneously in separate compositions, or sequentially in separate compositions) of a cytosine methylation inhibitor and an NF-κB activator is greater than the sum of the effects of each agent given alone.

In some embodiments, the magnitude of immunodeficiency virus reactivation after contacting an immunodeficiency virus-infected cell with a cytosine methylation inhibitor and an NF-κB activator is at least about 2.5-fold, 5-fold, at least about 10-fold, at least about 15-fold, at least about 20-fold, at least about 25-fold, at least about 30-fold, at least about 40-fold, at least about 50-fold, or more than 50-fold, greater than the additive effect of the cytosine methylation inhibitor or the NF-κB activator alone in reactivating latent immunodeficiency virus.

An effective amount of a cytosine methylation inhibitor and an NF-κB activator that reactivates latent HIV is an amount that reactivates latent HIV and reduces the reservoir of latent HIV in an individual by at least about 20%, at least about 30%, at least about 40%, at least about 50%, at least about 60%, at least about 70%, at least about 80%, or at least about 90%. A "reduction in the reservoir of latent HIV" (also referred to as "reservoir of latently infected cells") is a reduction in the number of cells in the individual that harbor a latent HIV infection. Whether the reservoir of latently infected cells is reduced can be determined using any known method, including the method described in Blankson et al. (2000) *J. Infect. Disease* 182(6):1636-1642.

In some embodiments, a subject method of treating an immunodeficiency virus infection in an individual in need thereof involves: a) administering to the individual a synergistically effective amount of an inhibitor of cytosine methylation and an NF-κB activator; and b) administering to the individual an effective amount of an agent that inhibits an immunodeficiency virus function. The immunodeficiency virus function can be selected from viral replication, viral protease activity, viral reverse transcriptase activity, viral entry into a cell, viral integrase activity, viral Rev activity, viral Tat activity, viral Nef activity, viral Vpr activity, viral Vpu activity, and viral Vif activity. Administering to the individual a synergistically effective amount of an inhibitor of cytosine methylation and an NF-κB activator results in reactivation of latent immunodeficiency virus. Administering an agent that inhibits an immunodeficiency virus function can result in one or both of: a reduction of immunodeficiency virus load in the individual; and an increase in the number of CD4$^+$ T cells in the individual.

Any of a variety of methods can be used to determine whether a treatment method is effective. For example, methods of determining whether the methods of the invention are effective in reducing immunodeficiency virus (e.g., HIV) viral load, and/or treating an immunodeficiency virus (e.g., HIV) infection, are any known test for indicia of immunodeficiency virus (e.g., HIV) infection, including, but not limited to, measuring viral load, e.g., by measuring the amount of immunodeficiency virus (e.g., HIV) in a biological sample, e.g., using a polymerase chain reaction (PCR) with primers specific for an immunodeficiency virus (e.g., HIV) polynucleotide sequence; detecting and/or measuring a polypeptide encoded by an immunodeficiency virus (e.g., HIV), e.g., p24, gp120, reverse transcriptase, using, e.g., an immunological assay such as an enzyme-linked immunosorbent assay (ELISA) with an antibody specific for the polypeptide; and measuring the CD4$^+$ T cell count in the individual.

Methods of assaying an HIV infection (or any indicia associated with an HIV infection) are known in the art, and have been described in numerous publications such as HIV Protocols (Methods in Molecular Medicine, 17) N. L. Michael and J. H. Kim, eds. (1999) Humana Press.

Cytosine Methylation Inhibitors

Suitable cytosine methylation inhibitors include, but are not limited to, zebularine ((1-(β-D-ribofuranosyl)-1,2-dihydropyrimidin-2-one); 5-aza-2' deoxycytidine (aza-CdR); procainamide; hydralazine; 1-β-D-arabinofuranosyl-5-azacytosine; 5,6-dihydro-5-azacytidine; 5-fluoro-2'-deoxycytidine (FdCyd); (–)-epigallocatechin-3-gallate (EGCG; [(2R,3R)-5,7-dihydroxy-2-(3,4,5-trihydroxyphenyl)chroman-3-yl]3,4,5-trihydroxybenzoate); psammaplin A (N,N"-(dithiodi-2,1-ethanediyl)bis[3-bromo-4-hydroxy-a-(hydroxyimino)-benzenepropanamide); 5-azacytidine (aza-C); and RG108 (2-(1,3-Dioxo-1,3-dihydro-2H-isoindol-2-yl)-3-(1H-indol-3-yl)propionic acid).

NF-κB Activators

Suitable activators of NF-κB include, but are not limited to, phytohemagglutinin (PHA); phorbol esters, e.g., tetradecanoyl phorbol acetate (TPA); lipopolysaccharide (LPF); tumor necrosis factor-α (TNFα); prostratin; TRAF family member-associated NFκB activator (TANK) polypeptide; IL-1β; and glutamate. Prostratin is (1aR,1bS,4aR,7aS,7bR,8R,9aS)-4-a,7b-dihydroxy-3-(hydroxymethyl)-1,1,6,8-tetramethyl-5-oxo-1,1a,1b,4,4a,5,7a,7b,8,9-decahydro-9aH-cyclopropa[3,4]benzo[1,2-e]azulen-9a-yl acetate; and is also known as 12-Deoxyphorbol-13-acetate. Also suitable for use is a prostratin analog. See, e.g., Wender et al. ((2008) Science 320:649) for prostratin analogs.

TANK polypeptides are known in the art and are suitable for use in a subject method. See, e.g., GenBank Accession Nos.: 1) NP_597841.1 (119 amino acids (aa); *Homo sapiens*) and corresponding GenBank Accession No. NM_133484, providing a nucleotide sequence encoding the amino acid sequence; 2) NP_004171.2 (425 aa; *Homo sapiens*) and corresponding GenBank Accession No. NM_004180, providing a nucleotide sequence encoding the amino acid sequence; 3) XP_001149930.1 (*Pan troglodytes*); 4) NP_001157544.1 (*Mus musculus*) and corresponding GenBank Accession No. NM_001164072, providing a nucleotide sequence encoding the amino acid sequence; 5) NP_001157545.1 (*Rattus norvegicus*) and corresponding GenBank Accession No. NM_001164073, providing a nucleotide sequence encoding the amino acid sequence; and 6) XP_001149721.1 (*Pan troglodytes*). A suitable TANK polypeptide includes a polypeptide comprising an amino acid sequence having at least about 85%, at least about 90%, at least about 95%, at least about 98%, at least about 99%, or 100%, amino acid sequence identity with any of the amino acid sequences provided at the aforementioned GenBank accession numbers. A suitable TANK polypeptide includes a polypeptide comprising an amino acid sequence having at least about 85%, at least about 90%, at least about 95%, at least about 98%, at least about 99%, or 100%, amino acid sequence identity a contiguous stretch of from about 100 amino acids to about 200 amino acids, from about 200 amino acids to about 300 amino acids, or from about 300 amino acids to 425 amino acids, of the amino acid sequence set forth in SEQ ID NO:27.

Amino acid sequences of TNF-α polypeptides from a variety of species are known and are suitable for use. See, e.g., GenBank Accession Nos.: 1) NP_000585 (*Homo sapiens*), and corresponding GenBank Accession No. NM_000594 for a nucleotide sequence encoding the amino acid sequence; 2) NP_001038976.1 (*Pan troglodytes*); 3) NP_001040614.1 (*Macaca mulatta*); 4) CAA47146.1 (*Rattus norvegicus*); and 5) NP_038721.1 (*Mus musculus*). A suitable TNF-α polypeptide includes a polypeptide comprising an amino acid sequence having at least about 85%, at least about 90%, at least about 95%, at least about 98%, at least about 99%, or 100%, amino acid sequence identity with any of the amino acid sequences provided at the aforementioned GenBank accession numbers. A suitable TNF-α polypeptide includes a polypeptide comprising an amino acid sequence having at least about 85%, at least about 90%, at least about 95%, at least about 98%, at least about 99%, or 100%, amino acid sequence identity with the amino acid sequence set forth in SEQ ID NO:1.

Combination Therapies

A synergistically effective amount of a cytosine methylation inhibitor and an NF-κb activator can be administered to an individual in combination (e.g., in the same formulation or in separate formulations) with another therapeutic agent ("combination therapy"). A synergistically effective amount of a cytosine methylation inhibitor and an NF-κb activator can be administered in admixture with another therapeutic agent or can be administered in a separate formulation. When administered in separate formulations, a synergistically effective amount of a cytosine methylation inhibitor and an NF-κb activator and another therapeutic agent can be administered substantially simultaneously (e.g., within about 60 minutes, about 50 minutes, about 40 minutes, about 30 minutes, about 20 minutes, about 10 minutes, about 5 minutes, or about 1 minute of each other) or separated in time by about 1 hour, about 2 hours, about 4 hours, about 6 hours, about 10 hours, about 12 hours, about 24 hours, about 36 hours, or about 72 hours, or more.

Any of a variety of methods can be used to determine whether a treatment method is effective. For example, methods of determining whether the methods of the invention are effective in reducing HIV load, and/or treating an HIV infection, are any known test for indicia of HIV infection, including, but not limited to, measuring viral load, e.g., by measuring the amount of HIV in a biological sample, e.g., using a polymerase chain reaction (PCR) with primers specific for an HIV polynucleotide sequence; detecting and/or measuring a polypeptide encoded by HIV, e.g., p24, gp120, reverse transcriptase, using, e.g., an immunological assay such as an enzyme-linked immunosorbent assay (ELISA) with an antibody specific for the polypeptide; and measuring the CD4$^+$ T cell count in the individual.

Formulations, Dosages, Routes of Administration

In general, active agents (e.g., a cytosine methylation inhibitor and an NF-κB activator) are prepared in a pharmaceutically acceptable composition(s) for delivery to a host. In some embodiments, a cytosine methylation inhibitor and an NF-κB activator are formulated separately in separate pharmaceutical compositions. In other embodiments, a cytosine methylation inhibitor and an NF-κB activator are formulated together in a single pharmaceutical composition. The terms "active agent," "drug," "agent," "therapeutic agent," and the like are used interchangeably herein. Pharmaceutically acceptable carriers preferred for use with active agents (e.g., a cytosine methylation inhibitor and an NF-κB activator; and optionally one or more additional therapeutic agent) may include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, and microparticles, including saline and buffered media. Parenteral vehicles include sodium chloride solution, Ringer's dextrose, dextrose and sodium chloride, lactated Ringer's or fixed oils. Intravenous vehicles include fluid and nutrient replenishers, electrolyte replenishers (such as those based on Ringer's dextrose), and the like. A composition comprising an active agent (e.g., a cytosine methylation inhibitor and an NF-κB activator; and optionally one or more additional therapeutic agent) may also be lyophilized using means well known in the art, for subsequent reconstitution and use according to the invention.

Formulations

Active agents (e.g., a cytosine methylation inhibitor and an NF-κB activator; and optionally one or more additional therapeutic agent) are administered to an individual in need thereof in a formulation with a pharmaceutically acceptable excipient(s). A wide variety of pharmaceutically acceptable excipients is known in the art and need not be discussed in detail herein. Pharmaceutically acceptable excipients have been amply described in a variety of publications, including, for example, A. Gennaro (2000) "Remington: The Science and Practice of Pharmacy", 20th edition, Lippincott, Williams, & Wilkins; Pharmaceutical Dosage Forms and Drug Delivery Systems (1999) H. C. Ansel et al., eds $7^{th}$ ed., Lippincott, Williams, & Wilkins; and Handbook of Pharmaceutical Excipients (2000) A. H. Kibbe et al., eds., $3^{rd}$ ed. Amer. Pharmaceutical Assoc. For the purposes of the following description of formulations, "active agent" includes a cytosine methylation inhibitor, an NF-κB activator, and optionally one or more additional therapeutic agent.

In a subject method, active agents (e.g., a cytosine methylation inhibitor and an NF-κB activator; and optionally one or more additional therapeutic agent) may be administered to the host using any convenient means capable of resulting in the desired degree of reactivation of latent immunodeficiency virus. Thus, active agents (e.g., a cytosine methylation inhibitor and an NF-κB activator; and optionally one or more additional therapeutic agent) can be incorporated into a variety of formulations for therapeutic administration. More particularly, active agents (e.g., a cytosine methylation inhibitor and an NF-κB activator; and optionally one or more additional therapeutic agent) can be formulated into pharmaceutical compositions by combination with appropriate, pharmaceutically acceptable carriers or diluents, and may be formulated into preparations in solid, semi-solid, liquid or gaseous forms, such as tablets, capsules, powders, granules, ointments, solutions, suppositories, injections, inhalants and aerosols. In an exemplary embodiment, an active agent (e.g., a cytosine methylation inhibitor, an NF-κB activator; and optionally one or more additional therapeutic agent) is formulated as a gel, as a solution, or in some other form suitable for intravaginal administration. In a further exemplary embodiment, an active agent (e.g., a cytosine methylation inhibitor, an NF-κB activator; and optionally one or more additional therapeutic agent) is formulated as a gel, as a solution, or in some other form suitable for rectal (e.g., intrarectal) administration.

In pharmaceutical dosage forms, an active agent (e.g., a cytosine methylation inhibitor, an NF-κB activator; and optionally one or more additional therapeutic agent) may be administered in the form of its pharmaceutically acceptable salts, or it may also be used alone or in appropriate association, as well as in combination, with other pharmaceutically active compounds. The following methods and excipients are merely exemplary and are in no way limiting.

In some embodiments, an agent (e.g., a cytosine methylation inhibitor, an NF-κB activator; and optionally one or more additional therapeutic agent) is formulated in an aqueous buffer. Suitable aqueous buffers include, but are not limited to, acetate, succinate, citrate, and phosphate buffers varying in strengths from about 5 mM to about 100 mM. In some embodiments, the aqueous buffer includes reagents that provide for an isotonic solution. Such reagents include, but are not limited to, sodium chloride; and sugars e.g., mannitol, dextrose, sucrose, and the like. In some embodiments, the aqueous buffer further includes a non-ionic surfactant such as polysorbate 20 or 80. Optionally the formulations may further include a preservative. Suitable preservatives include, but are not limited to, a benzyl alcohol, phenol, chlorobutanol, benzalkonium chloride, and the like. In many cases, the formulation is stored at about 4° C. Formulations may also be lyophilized, in which case they generally include cryoprotectants such as sucrose, trehalose, lactose, maltose, mannitol, and the like. Lyophilized formulations can be stored over extended periods of time, even at ambient temperatures.

For oral preparations, an active agent (e.g., a cytosine methylation inhibitor, an NF-κB activator; and optionally one or more additional therapeutic agent) can be used alone or in combination with appropriate additives to make tablets, powders, granules or capsules, for example, with conventional additives, such as lactose, mannitol, corn starch or potato starch; with binders, such as crystalline cellulose, cellulose derivatives, acacia, corn starch or gelatins; with disintegrators, such as corn starch, potato starch or sodium carboxymethylcellulose; with lubricants, such as talc or magnesium stearate; and if desired, with diluents, buffering agents, moistening agents, preservatives and flavoring agents.

An active agent (e.g., a cytosine methylation inhibitor, an NF-κB activator; and optionally one or more additional therapeutic agent) can be formulated into preparations for injection by dissolving, suspending or emulsifying them in an aqueous or nonaqueous solvent, such as vegetable or other similar oils, synthetic aliphatic acid glycerides, esters of higher aliphatic acids or propylene glycol; and if desired, with conventional additives such as solubilizers, isotonic agents, suspending agents, emulsifying agents, stabilizers and preservatives.

An active agent (e.g., a cytosine methylation inhibitor, an NF-κB activator; and optionally one or more additional therapeutic agent) can be utilized in aerosol formulation to be administered via inhalation. An active agent (e.g., a cytosine methylation inhibitor, an NF-κB activator; and optionally one or more additional therapeutic agent) can be formulated into pressurized acceptable propellants such as dichlorodifluoromethane, propane, nitrogen and the like.

Furthermore, an active agent can be made into suppositories by mixing with a variety of bases such as emulsifying bases or water-soluble bases. An active agent can be administered rectally via a suppository. The suppository can include vehicles such as cocoa butter, carbowaxes and polyethylene glycols, which melt at body temperature, yet are solidified at room temperature.

Unit dosage forms for oral or rectal administration such as syrups, elixirs, and suspensions may be provided wherein each dosage unit, for example, teaspoonful, tablespoonful, tablet or suppository, contains a predetermined amount of the composition containing one or more active agents. Similarly, unit dosage forms for injection or intravenous administration may comprise the active agent(s) in a composition as a solution in sterile water, normal saline or another pharmaceutically acceptable carrier.

Unit dosage forms for intravaginal or intrarectal administration such as syrups, elixirs, gels, and suspensions may be provided wherein each dosage unit, for example, teaspoonful, tablespoonful, tablet, unit gel volume, or suppository, contains a predetermined amount of the composition containing one or more active agents.

The term "unit dosage form," as used herein, refers to physically discrete units suitable as unitary dosages for human and animal subjects, each unit containing a predetermined quantity of an active agent, calculated in an amount sufficient to produce the desired effect in association with a pharmaceutically acceptable diluent, carrier or vehicle. The specifications for a given active agent will depend in part on the particular compound employed and the effect to be achieved, and the pharmacodynamics associated with each compound in the host.

Other modes of administration will also find use with the subject invention. For instance, an active agent can be formulated in suppositories and, in some cases, aerosol and intranasal compositions. For suppositories, the vehicle composition will include traditional binders and carriers such as, polyalkylene glycols, or triglycerides. Such suppositories may be formed from mixtures containing the active ingredient in the range of about 0.5% to about 10% (w/w), e.g. about 1% to about 2%.

An active agent can be administered as injectables. Typically, injectable compositions are prepared as liquid solutions or suspensions; solid forms suitable for solution in, or suspension in, liquid vehicles prior to injection may also be prepared. The preparation may also be emulsified or the active ingredient encapsulated in liposome vehicles.

An active agent will in some embodiments be formulated for vaginal delivery. A subject formulation for intravaginal administration is formulated as an intravaginal bioadhesive tablet, intravaginal bioadhesive microparticle, intravaginal cream, intravaginal lotion, intravaginal foam, intravaginal ointment, intravaginal paste, intravaginal solution, or intravaginal gel.

An active agent will in some embodiments be formulated for rectal delivery. A subject formulation for intrarectal administration is formulated as an intrarectal bioadhesive tablet, intrarectal bioadhesive microparticle, intrarectal cream, intrarectal lotion, intrarectal foam, intrarectal ointment, intrarectal paste, intrarectal solution, or intrarectal gel.

A subject formulation comprising an active agent includes one or more of an excipient (e.g., sucrose, starch, mannitol, sorbitol, lactose, glucose, cellulose, talc, calcium phosphate or calcium carbonate), a binder (e.g., cellulose, methylcellulose, hydroxymethylcellulose, polypropylpyrrolidone, polyvinylprrolidone, gelatin, gum arabic, polyethyleneglycol, sucrose or starch), a disintegrator (e.g., starch, carboxymethylcellulose, hydroxypropylstarch, low substituted hydroxypropylcellulose, sodium bicarbonate, calcium phosphate or calcium citrate), a lubricant (e.g., magnesium stearate, light anhydrous silicic acid, talc or sodium lauryl sulfate), a flavoring agent (e.g., citric acid, menthol, glycine or orange powder), a preservative (e.g., sodium benzoate, sodium bisulfite, methylparaben or propylparaben), a stabilizer (e.g., citric acid, sodium citrate or acetic acid), a suspending agent (e.g., methylcellulose, polyvinylpyrrolidone or aluminum stearate), a dispersing agent (e.g., hydroxypropylmethylcellulose), a diluent (e.g., water), and base wax (e.g., cocoa butter, white petrolatum or polyethylene glycol).

Tablets comprising an active agent may be coated with a suitable film-forming agent, e.g., hydroxypropylmethyl cellulose, hydroxypropyl cellulose or ethyl cellulose, to which a suitable excipient may optionally be added, e.g., a softener such as glycerol, propylene glycol, diethylphthalate, or glycerol triacetate; a filler such as sucrose, sorbitol, xylitol, glucose, or lactose; a colorant such as titanium hydroxide; and the like.

Suitable excipient vehicles are, for example, water, saline, dextrose, glycerol, ethanol, or the like, and combinations thereof. In addition, if desired, the vehicle may contain minor amounts of auxiliary substances such as wetting or emulsifying agents or pH buffering agents. Actual methods of preparing such dosage forms are known, or will be apparent, to those skilled in the art. See, e.g., Remington's Pharmaceutical Sciences, Mack Publishing Company, Easton, Pa., 17th edition, 1985. The composition or formulation to be administered will, in any event, contain a quantity of the agent adequate to achieve the desired state in the subject being treated.

The pharmaceutically acceptable excipients, such as vehicles, adjuvants, carriers or diluents, are readily available to the public. Moreover, pharmaceutically acceptable auxiliary substances, such as pH adjusting and buffering agents, tonicity adjusting agents, stabilizers, wetting agents and the like, are readily available to the public.

As noted above, in some embodiments, a cytosine methylation inhibitor and an NF-κB activator are formulated in a single pharmaceutical composition. Thus, the present disclosure provides a pharmaceutical composition comprising: a) an inhibitor of cytosine methylation; b) an NF-κB activator; and c) a pharmaceutically acceptable carrier, where the inhibitor of cytosine methylation and the NF-κB activator are present in amounts effective to synergistically reactivate latent immunodeficiency virus in an immunodeficiency virus-infected cell.

Dosages

Although the dosage used will vary depending on the clinical goals to be achieved, a suitable dosage range is one which provides up to about 1 mg to about 1000 mg, e.g., from about 1 mg to about 25 mg, from about 25 mg to about 50 mg, from about 50 mg to about 100 mg, from about 100 mg to about 200 mg, from about 200 mg to about 250 mg, from about 250 mg to about 500 mg, or from about 500 mg to about 1000 mg of an active agent (e.g., a cytosine methylation inhibitor, an NF-κB activator; and optionally one or more additional therapeutic agent) can be administered in a single dose.

Those of skill will readily appreciate that dose levels can vary as a function of the specific compound, the severity of the symptoms and the susceptibility of the subject to side effects. Preferred dosages for a given compound are readily determinable by those of skill in the art by a variety of means.

In some embodiments, a single dose of an active agent (e.g., a cytosine methylation inhibitor, an NF-κB activator; and optionally one or more additional therapeutic agent) is administered. In other embodiments, multiple doses of an active agent (e.g., a cytosine methylation inhibitor, an NF-κB activator; and optionally one or more additional therapeutic agent) are administered. Where multiple doses are administered over a period of time, an active agent is administered twice daily (qid), daily (qd), every other day (qod), every third day, three times per week (tiw), or twice per week (biw) over a period of time. For example, an active agent is administered qid, qd, qod, tiw, or biw over a period of from one day to about 2 years or more. For example, an active agent is administered at any of the aforementioned frequencies for one week, two weeks, one month, two months, six months, one year, or two years, or more, depending on various factors.

A cytosine methylation inhibitor and an NF-κB activator can be administered in separate formulations. A cytosine methylation inhibitor and an NF-κB activator can be administered substantially simultaneously, or within about 30 minutes, about 1 hour, about 2 hours, about 4 hours, about 8 hours, about 16 hours, about 24 hours, about 36 hours, about 72 hours, about 4 days, about 7 days, or about 2 weeks of one another.

Routes of Administration

An active agent (e.g., a cytosine methylation inhibitor, an NF-κB activator; and optionally one or more additional therapeutic agent) is administered to an individual using any available method and route suitable for drug delivery, including in vivo and ex vivo methods, as well as systemic and localized routes of administration.

Conventional and pharmaceutically acceptable routes of administration include intranasal, intramuscular, intratracheal, transdermal, subcutaneous, intradermal, topical application, intravenous, vaginal, nasal, and other parenteral routes of administration. In some embodiments, an active agent is administered via an intravaginal route of administration. In other embodiments, an active agent is administered via an intrarectal route of administration. Routes of administration may be combined, if desired, or adjusted depending upon the agent and/or the desired effect. The composition can be administered in a single dose or in multiple doses.

An active agent (e.g., a cytosine methylation inhibitor, an NF-κB activator; and optionally one or more additional therapeutic agent) can be administered to a host using any available conventional methods and routes suitable for delivery of conventional drugs, including systemic or localized routes. In general, routes of administration contemplated by the invention include, but are not necessarily limited to, enteral, parenteral, or inhalational routes.

Parenteral routes of administration other than inhalation administration include, but are not necessarily limited to, topical, vaginal, transdermal, subcutaneous, intramuscular, and intravenous routes, i.e., any route of administration other than through the alimentary canal. Parenteral administration can be carried to effect systemic or local delivery of the agent. Where systemic delivery is desired, administration typically involves invasive or systemically absorbed topical or mucosal administration of pharmaceutical preparations.

An active agent (e.g., a cytosine methylation inhibitor, an NF-κB activator; and optionally one or more additional therapeutic agent) can also be delivered to the subject by enteral administration. Enteral routes of administration include, but are not necessarily limited to, oral and rectal (e.g., using a suppository) delivery.

By treatment is meant at least an amelioration of the symptoms associated with the pathological condition afflicting the host, where amelioration is used in a broad sense to refer to at least a reduction in the magnitude of a parameter, e.g. symptom, associated with the pathological condition being treated, such as the number of viral particles per unit blood. As such, treatment also includes situations where the pathological condition, or at least symptoms associated therewith, are completely inhibited, e.g. prevented from happening, or stopped, e.g. terminated, such that the host no longer suffers from the pathological condition, or at least the symptoms that characterize the pathological condition.

A variety of hosts (wherein the term "host" is used interchangeably herein with the terms "subject" and "patient") are treatable according to the subject methods. Generally such hosts are "mammals" or "mammalian," where these terms are used broadly to describe organisms which are within the class mammalia, and primates (e.g., humans, chimpanzees, and monkeys), that are susceptible to immunodeficiency virus (e.g., HIV) infection. In many embodiments, the hosts will be humans.

Combination Therapies

A cytosine methylation inhibitor and an NF-κB activator can be administered to an individual in combination (e.g., in the same formulation or in separate formulations) with at least one additional therapeutic agent ("combination therapy"). A cytosine methylation inhibitor and an NF-κB activator can be administered in admixture with at least one additional therapeutic agent or can be administered in separate formulations. When administered in separate formulations, a cytosine methylation inhibitor, an NF-κB activator, and at least one additional therapeutic agent can be administered substantially simultaneously (e.g., within about 60 minutes, about 50 minutes, about 40 minutes, about 30 minutes, about 20 minutes, about 10 minutes, about 5 minutes, or about 1 minute of each other) or separated in time by about 1 hour, about 2 hours, about 4 hours, about 6 hours, about 10 hours, about 12 hours, about 24 hours, about 36 hours, or about 72 hours, or more. Effective amounts of a cytosine methylation inhibitor and an NF-κB activator are as described above.

Therapeutic agents that can be administered in combination therapy with a cytosine methylation inhibitor and an NF-κB activator include, e.g., anti-inflammatory, anti-viral, anti-fungal, anti-mycobacterial, antibiotic, amoebicidal, trichomonocidal, analgesic, anti-neoplastic, anti-hypertensives, anti-microbial and/or steroid drugs, to treat viral infections. In some embodiments, patients with a viral or bacterial infection are treated with a combination of a cytosine methylation inhibitor and an NF-κB activator, and one or more of the following; beta-lactam antibiotics, tetracyclines, chloramphenicol, neomycin, gramicidin, bacitracin, sulfonamides, nitrofurazone, nalidixic acid, cortisone, hydrocortisone, betamethasone, dexamethasone, fluocortolone, prednisolone, triamcinolone, indomethacin, sulindac, acyclovir, amantadine, rimantadine, recombinant soluble CD4 (rsCD4), anti-receptor antibodies (e.g., for rhinoviruses), nevirapine, cidofovir (Vistide™), trisodium phosphonoformate (Foscarnet™), famcyclovir, pencyclovir, valacyclovir, nucleic acid/replication inhibitors, interferon, zidovudine (AZT, Retrovir™), zidovudine/lamivudine (Combivir), didanosine (dideoxyinosine, ddI, Videx™), stavudine (d4T, Zerit™), zalcitabine (dideoxycytosine, ddC, Hivid™) nevirapine (Viramune™), lamivudine (Epivir™, 3TC), protease inhibitors, saquinavir (Invirase™, Fortovase™), ritonavir (Norvir™), nelfinavir (Viracept™), efavirenz (Sustiva™), abacavir (Ziagen™), amprenavir (Agenerase™) indinavir (Crixivan™) ganciclovir, AzDU, delavirdine (Rescriptor™), lopinavir/ritonavir (Kaletra), trizivir, rifampin, clathiromycin, erythropoietin, colony stimulating factors (G-CSF and GM-CSF), non-nucleoside reverse transcriptase inhibitors, nucleoside inhibitors, adriamycin, fluorouracil, methotrexate, asparaginase and combinations thereof. Anti-HIV agents are those in the preceding list that specifically target a function of one or more HIV proteins.

In some embodiments, a synergistically effective amount of a cytosine methylation inhibitor and an NF-κB activator is administered in combination therapy with two or more anti-HIV agents. For example, a synergistically effective amount of a cytosine methylation inhibitor and an NF-κB activator can be administered in combination therapy with one, two, or three nucleoside reverse transcriptase inhibitors (e.g., Combivir, Epivir, Hivid, Retrovir, Videx, Zerit, Ziagen, etc.). A synergistically effective amount of a cytosine methylation inhibitor and an NF-κB activator can be administered in combination therapy with one or two non-nucleoside reverse transcriptase inhibitors (e.g., Rescriptor, Sustiva, Viramune, etc.). A synergistically effective amount of a cytosine methylation inhibitor and an NF-κB activator can be administered in combination therapy with one or two protease inhibitors (e.g., Agenerase, Crixivan, Fortovase, Invirase, Kaletra, Norvir, Viracept, etc.). A synergistically effective amount of a cytosine methylation inhibitor and an NF-κB activator can be administered in combination therapy with a protease inhibitor and a nucleoside reverse transcriptase inhibitor. A synergistically effective amount of a cytosine methylation inhibitor and an NF-κB activator can be administered in combination therapy with a protease inhibitor, a nucleoside reverse transcriptase inhibitor, and a non-nucleoside reverse transcriptase inhibitor. A synergistically effective amount of a cytosine methylation inhibitor and an NF-κB activator can be administered in combination therapy with a protease inhibitor and a non-nucleoside reverse transcriptase inhibitor. Other combinations of a synergistically effective amount of a cytosine methylation inhibitor and an NF-κB activator with one or more of a protease inhibitor, a nucleoside reverse transcriptase inhibitor, and a non-nucleoside reverse transcriptase inhibitor are contemplated.

In some embodiments, a subject treatment method involves administering: a) a synergistically effective amount of a cytosine methylation inhibitor and an NF-κB activator; and b) an agent that inhibits an immunodeficiency virus function selected from viral replication, viral protease activity, viral reverse transcriptase activity, viral entry into a cell, viral integrase activity, viral Rev activity, viral Tat activity, viral Nef activity, viral Vpr activity, viral Vpu activity, and viral Vif activity.

In some embodiments, a subject treatment method involves administering: a) a synergistically effective amount of a cytosine methylation inhibitor and an NF-κB activator; and b) an HIV inhibitor, where suitable HIV inhibitors include, but are not limited to, one or more nucleoside/nucleotide reverse transcriptase inhibitors (NRTIs), non-nucleoside reverse transcriptase inhibitors (NNRTIs), protease inhibitors (PIs), fusion inhibitors, integrase inhibitors, chemokine receptor (e.g., CXCR4, CCR5) inhibitors, and hydroxyurea.

Nucleoside reverse transcriptase inhibitors include, but are not limited to, abacavir (ABC; ZIAGEN™), didanosine (dideoxyinosine (ddI); VIDEX™), lamivudine (3TC; EPIVIR™), stavudine (d4T; ZERIT™, ZERIT XR™), zalcitabine (dideoxycytidine (ddC); HIVID™), zidovudine (ZDV, formerly known as azidothymidine (AZT); RETROVIR™), abacavir, zidovudine, and lamivudine (TRIZIVIRT™), zidovudine and lamivudine (COMBIVIR™), and emtricitabine (EMTRIVA™). Nucleotide reverse transcriptase inhibitors include tenofovir disoproxil fumarate (VIREAD™). Non-nucleoside reverse transcriptase inhibitors for HIV include, but are not limited to, nevirapine (VIRAMUNE™), delavirdine mesylate (RESCRIPTOR™), and efavirenz (SUSTIVAT™).

Protease inhibitors (PIs) for treating HIV infection include amprenavir (AGENERASE™), saquinavir mesylate (FORTOVASET™, INVIRASE™.), ritonavir (NORVIR™), indinavir sulfate (CRIXIVAN™), nelfmavir mesylate (VIRACEPTT™), lopinavir and ritonavir (KALETRA™), atazanavir (REYATAZ™), and fosamprenavir (LEXIVA™).

Fusion inhibitors prevent fusion between the virus and the cell from occurring, and therefore, prevent HIV infection and multiplication. Fusion inhibitors include, but are not limited to, enfuvirtide (FUZEON™), Lalezari et al., New England J. Med., 348:2175-2185 (2003); and maraviroc (SELZENTRY™, Pfizer).

An integrase inhibitor blocks the action of integrase, preventing HIV-1 genetic material from integrating into the host DNA, and thereby stopping viral replication. Integrase inhibitors include, but are not limited to, raltegravir (ISENTRESS™, Merck); and elvitegravir (GS 9137, Gilead Sciences).

Maturation inhibitors include, e.g., bevirimat (3β-(3-carboxy-3-methyl-butanoyloxy) lup-20(29)-en-28-oic acid); and Vivecon (MPC9055).

In some embodiments, a subject treatment method involves administering: a) a synergistically effective amount of a cytosine methylation inhibitor and an NF-κB activator; and b) one or more of: (1) an HIV protease inhibitor selected from amprenavir, atazanavir, fosamprenavir, indinavir, lopinavir, ritonavir, nelfinavir, saquinavir, tipranavir, brecanavir, darunavir, TMC-126, TMC-114, mozenavir (DMP-450), JE-2147 (AG1776), L-756423, R00334649, KNI-272, DPC-681, DPC-684, GW640385X, DG17, PPL-100, DG35, and AG 1859; (2) an HIV non-nucleoside inhibitor of reverse transcriptase selected from capravirine, emivirine, delavirdine, efavirenz, nevirapine, (+) calanolide A, etravirine, GW5634, DPC-083, DPC-961, DPC-963, MIV-150, and TMC-120, TMC-278 (rilpivirene), efavirenz, BILR 355 BS, VRX 840773, UK-453061, and RDEA806; (3) an HIV nucleoside inhibitor of reverse transcriptase selected from zidovudine, emtricitabine, didanosine, stavudine, zalcitabine, lamivudine, abacavir, amdoxovir, elvucitabine, alovudine, MIV-210, racivir (@-FTC), D-d4FC, emtricitabine, phosphazide, fozivudine tidoxil, apricitibine (AVX754), amdoxovir, KP-1461, and fosalvudine tidoxil (formerly HDP 99.0003); (4) an HIV nucleotide inhibitor of reverse transcriptase selected from tenofovir and adefovir; (5) an HIV integrase inhibitor selected from curcumin, derivatives of curcumin, chicoric acid, derivatives of chicoric acid, 3,5-dicaffeoylquinic acid, derivatives of 3,5-dicaffeoylquinic acid, aurintricarboxylic acid, derivatives of aurintricarboxylic acid, caffeic acid phenethyl ester, derivatives of caffeic acid phenethyl ester, tyrphostin, derivatives of tyrphostin, quercetin, derivatives of quercetin, S-1360, zintevir (AR-177), L-870812, and L-870810, MK-0518 (raltegravir), BMS-538158, GSK364735C, BMS-707035, MK-2048, and BA 011; (6) a gp41 inhibitor selected from enfuvirtide, sifuvirtide, FB006M, and TRI-1144; (7) a CXCR4 inhibitor, such as AMD-070; (8) an entry inhibitor, such as SP01A; (9) a gp120 inhibitor, such as BMS-488043 and/or BlockAide/CR; (10) a G6PD and NADH-oxidase inhibitor, such as immunitin; (11) a CCR5 inhibitors selected from the group consisting of aplaviroc, vicriviroc, maraviroc, PRO-140, INCB15050, PF-232798 (Pfizer), and CCR5 mAb004; (12) another drug for treating HIV selected from BAS-100, SPI-452, REP 9, SP-01A, TNX-355, DES6, ODN-93, ODN-112, VGV-1, PA-457 (bevirimat), Ampligen, HRG214, Cytolin, VGX-410, KD-247, AMZ 0026, CYT 99007A-221 HIV, DEBIO-025, BAY 50-4798, MDX010 (ipilimumab), PBS119, ALG 889, and PA-1050040 (PA-040); (13) any combinations or mixtures of the above.

For example, in some embodiments, a subject treatment method involves administering: a) a synergistically effective amount of a cytosine methylation inhibitor and an NF-κB activator; and b) one or more of: i) amprenavir (Agenerase; (3S)-oxolan-3-yl  N-[(2S,3R)-3-hydroxy-4-[N-(2-methylpropyl)(4-aminobenzene)sulfonamido]-1-phenylbutan-2-yl] carbamate) in an amount of 600 mg or 1200 mg twice daily; ii) tipranavir (Aptivus; N-{3-[(1R)-1-[(2R)-6-hydroxy-4-oxo-2-(2-phenylethyl)-2-propyl-3,4-dihydro-2H-pyran-5-yl]propyl]phenyl}-5-(trifluoromethyl)pyridine-2-sulfonamide) in an amount of 500 mg twice daily; iii) idinavir (Crixivan; (2S)-1-[(2S,4R)-4-benzyl-2-hydroxy-4-{[(1S, 2R)-2-hydroxy-2,3-dihydro-1H-inden-1-yl] carbamoyl}butyl]-N-tert-butyl-4-(pyridin-3-ylmethyl)piperazine-2-carboxamide) in an amount of 800 mg three times daily; iv) saquinavir (Invirase; 2S)—N-[(2S,3R)-4-[(3S)-3-(tert-butylcarbamoyl)-decahydroisoquinolin-2-yl]-3-hydroxy-1-phenylbutan-2-yl]-2-(quinolin-2-ylformamido)butanediamide) in an amount of 1,000 mg twice daily; v) lopinavir and ritonavir (Kaleta; where lopinavir is 2S)—N-[(2S,4S,5S)-5-[2-(2,6-dimethylphenoxy)acetamido]-4-hydroxy-1,6-diphenylhexan-2-yl]-3-methyl-2-(2-oxo-1,3-diazinan-1-yl)butanamide; and ritonavir is 1,3-thiazol-5-ylmethyl N-[(2S,3S,5S)-3-hydroxy-5-[(2S)-3-methyl-2-{[methyl({[2-(propan-2-yl)-1,3-thiazol-4-yl]methyl})carbamoyl]amino}butanamido]-1,6-diphenylhexan-2-yl]carbamate) in an amount of 133 mg twice daily; vi) fosamprenavir (Lexiva; {[(2R,3S)-1-[N-(2-methylpropyl)(4-aminobenzene)sulfonamido]-3-({[(3S)-oxolan-3-yloxy] carbonyl}amino)-4-phenylbutan-2-yl]oxy}phosphonic acid) in an amount of 700 mg or 1400 mg twice daily); vii) ritonavir (Norvir) in an amount of 600 mg twice daily; viii) nelfinavir (Viracept; (3S,4aS,8aS)—N-tert-butyl-2-[(2R, 3R)-2-hydroxy-3-[(3-hydroxy-2-methylphenyl)formamido]-4-(phenylsulfanyl)butyl]-decahydroisoquinoline-3-carboxamide) in an amount of 750 mg three times daily or in an amount of 1250 mg twice daily; ix) Fuzeon (Acetyl-YTSLIHSLIEESQNQQEKNEQELLELDKWASLWNWF-amide) (SEQ ID NO:3) in an amount of 90 mg twice daily; x) Combivir in an amount of 150 mg lamivudine (3TC; 2',3'-dideoxy-3'-thiacytidine) and 300 mg zidovudine (AZT; azidothymidine) twice daily; xi) emtricitabine (Emtriva; 4-amino-5-fluoro-1-[(2R,5S)-2-(hydroxymethyl)-1,3-oxathiolan-5-yl]-1,2-dihydropyrimidin-2-one) in an amount of 200 mg once daily; xii) Epzicom in an amount of 600 mg abacavir (ABV; {(1S,4R)-4-[2-amino-6-(cyclopropylamino)-9H-purin-9-yl]cyclopent-2-en-1-yl}methanol) and 300 mg 3TC once daily; xiii) zidovudine (Retrovir; AZT or azidothymidine) in an amount of 200 mg three times daily; xiv) Trizivir in an amount of 150 mg 3TC and 300 mg ABV and 300 mg AZT twice daily; xv) Truvada in an amount of 200 mg emtricitabine and 300 mg tenofovir (({[(2R)-1-(6-amino-9H-purin-9-yl)propan-2-yl]oxy}methyl)phosphonic acid) once daily; xvi) didanosine (Videx; 2',3'-dideoxyinosine) in an amount of 400 mg once daily; xvii) tenofovir (Viread) in an amount of 300 mg once daily; xviii) abacavir (Ziagen) in an amount of 300 mg twice daily; xix) atazanavir (Reyataz; methyl N-[(1S)-1-{[(2S,3S)-3-hydroxy-4-[(2S)-2-[(methoxycarbonyl)amino]-3,3-dimethyl-N'-{[4-(pyridin-2-yl)phenyl]methyl}butanehydrazido]-1-phenylbutan-2-yl] carbamoyl}-2,2-dimethylpropyl]carbamate) in an amount of 300 mg once daily or 400 mg once daily; xx) lamivudine (Epivir) in an amount of 150 mg twice daily; xxi) stavudine (Zerit; 2'-3'-didehydro-2'-3'-dideoxythymidine) in an amount of 40 mg twice daily; xxii) delavirdine (Rescriptor; N-[2-({4-[3-(propan-2-ylamino)pyridin-2-yl]piperazin-1-yl}carbonyl)-1H-indol-5-yl]methanesulfonamide) in an amount of 400 mg three times daily; xxiii) efavirenz (Sustiva; (4S)-6-chloro-4-(2-cyclopropylethynyl)-4-(trifluoromethyl)-2,4-dihydro-1H-3,1-benzoxazin-2-one) in an amount of 600 mg once daily); xxiv) nevirapine (Viramune; 11-cyclopropyl-4-methyl-5,11-dihydro-6H-dipyrido[3,2-b:2',3'-e] [1,4]diazepin-6-one) in an amount of 200 mg twice daily); xxv) bevirimat; and xxvi) Vivecon.

Kits, Containers, Devices, Delivery Systems

Kits with unit doses (e.g., synergistically effective doses) of a cytosine methylation inhibitor and an NF-κB activator, e.g. in oral, vaginal, rectal, transdermal, or injectable doses (e.g., for intramuscular, intravenous, or subcutaneous injection), are provided. In such kits, in addition to the containers containing the unit doses will be an informational package insert describing the use and attendant benefits of the drugs in treating an immunodeficiency virus (e.g., HIV) infection. Suitable active agents and unit doses are those described herein above.

In many embodiments, a subject kit will further include instructions for practicing the subject methods or means for obtaining the same (e.g., a website URL directing the user to a webpage which provides the instructions), where these instructions are typically printed on a substrate, which substrate may be one or more of: a package insert, the packaging, formulation containers, and the like.

In some embodiments, a subject kit includes one or more components or features that increase patient compliance, e.g., a component or system to aid the patient in remembering to take the active agent at the appropriate time or interval. Such components include, but are not limited to, a calendaring system to aid the patient in remembering to take the active agent at the appropriate time or interval.

The present disclosure provides a delivery system comprising an active agent that inhibits cytosine methylation and an agent that is an NF-κB activator, where the combination of the two agents synergistically reactivate latent immunodeficiency virus in an immunodeficiency virus-infected cell. In some embodiments, the delivery system is a delivery system that provides for injection of a formulation comprising an active agent subcutaneously, intravenously, or intramuscularly. In other embodiments, the delivery system is a vaginal or rectal delivery system.

In some embodiments, a cytosine methylation inhibitor and an NF-κB activator are packaged for oral administration. The present disclosure provides a packaging unit comprising daily dosage units of a cytosine methylation inhibitor and an NF-κB activator, in separate formulations or co-formulated. For example, the packaging unit is in some embodiments a conventional blister pack or any other form that includes tablets, pills, and the like. The blister pack will contain the appropriate number of unit dosage forms, in a sealed blister pack with a cardboard, paperboard, foil, or plastic backing, and enclosed in a suitable cover. Each blister container may be numbered or otherwise labeled, e.g., starting with day 1.

In some embodiments, a subject delivery system comprises an injection device. Exemplary, non-limiting drug delivery devices include injections devices, such as pen injectors, and needle/syringe devices. In some embodiments, the present disclosure provides an injection delivery device that is pre-loaded with a formulation comprising synergistically effective amounts of a cytosine methylation inhibitor and an NF-κB activator. For example, a subject delivery device comprises an injection device pre-loaded with a single dose of a cytosine methylation inhibitor and an NF-κB activator. A subject injection device can be re-usable or disposable.

Pen injectors are well known in the art. Exemplary devices which can be adapted for use in the present methods are any of a variety of pen injectors from Becton Dickinson, e.g., BD™ Pen, BD™ Pen II, BD™ Auto-Injector; a pen injector from Innoject, Inc.; any of the medication delivery pen devices discussed in U.S. Pat. Nos. 5,728,074, 6,096, 010, 6,146,361, 6,248,095, 6,277,099, and 6,221,053; and the like. The medication delivery pen can be disposable, or reusable and refillable.

In some embodiments, the delivery system comprises a first container comprising a composition comprising a cytosine methylation inhibitor; and a second container comprising a composition comprising an NF-κB activator. The first and second containers can be, e.g., syringes. The delivery system can further comprise needles for use together with the syringes. The present disclosure provides a device comprising a first container comprising a composition comprising a cytosine methylation inhibitor; and a second container comprising a composition comprising an NF-κB activator. The first and second containers can be, e.g., syringes.

The present disclosure provides a delivery system for vaginal or rectal delivery of a cytosine methylation inhibitor and an NF-κB activator to the vagina or rectum of an individual. The delivery system comprises a device for insertion into the vagina or rectum. In some embodiments, the delivery system comprises an applicator for delivery of a formulation into the vagina or rectum; and a container that contains a formulation(s) comprising a cytosine methylation inhibitor and an NF-κB activator, where the cytosine methylation inhibitor and the NF-κB activator can be formulated separately or can be co-formulated. In these embodiments, the container (e.g., a tube) is adapted for delivering a formulation into the applicator. In other embodiments, the delivery system comprises a device that is inserted into the vagina or rectum, which device includes an active agent. For example, the device is coated with, impregnated with, or otherwise contains a formulation comprising the active agent.

In some embodiments, the vaginal or rectal delivery system is a tampon or tampon-like device that comprises a subject formulation. Drug delivery tampons are known in the art, and any such tampon can be used in conjunction with a subject drug delivery system. Drug delivery tampons are described in, e.g., U.S. Pat. No. 6,086,909 If a tampon or tampon-like device is used, there are numerous methods by which an active agent can be incorporated into the device. For example, the drug can be incorporated into a gel-like bioadhesive reservoir in the tip of the device. Alternatively, the drug can be in the form of a powdered material positioned at the tip of the tampon. The drug can also be absorbed into fibers at the tip of the tampon, for example, by dissolving the drug in a pharmaceutically acceptable carrier and absorbing the drug solution into the tampon fibers. The drug can also be dissolved in a coating material which is applied to the tip of the tampon. Alternatively, the drug can be incorporated into an insertable suppository which is placed in association with the tip of the tampon.

In other embodiments, the drug delivery device is a vaginal or rectal ring. Vaginal or rectal rings usually consist of an inert elastomer ring coated by another layer of elastomer containing an active agent to be delivered. The rings can be easily inserted, left in place for the desired period of time (e.g., up to 7 days), then removed by the user. The ring can optionally include a third, outer, rate-controlling elastomer layer which contains no drug. Optionally, the third ring can contain a second drug for a dual release ring. The drug can be incorporated into polyethylene glycol throughout the silicone elastomer ring to act as a reservoir for drug to be delivered.

In other embodiments, a subject vaginal or rectal delivery system is a vaginal or rectal sponge. An active agent(s) is incorporated into a silicone matrix which is coated onto a cylindrical drug-free polyurethane sponge, as described in the literature.

Pessaries, tablets and suppositories are other examples of drug delivery systems which can be used in connection with a subject treatment method. These systems have been described extensively in the literature.

Bioadhesive microparticles constitute still another drug delivery system suitable for use in the present invention. This system is a multi-phase liquid or semi-solid preparation which does not seep from the vagina or rectum as do many suppository formulations. The substances cling to the wall of the vagina or rectum and release the drug over a period of time. Many of these systems were designed for nasal use but can be used in the vagina or rectum as well (e.g. U.S. Pat. No. 4,756,907). The system may comprise microspheres with an active agent; and a surfactant for enhancing uptake of the drug. The microparticles have a diameter of 10 μm to 100 μm and can be prepared from starch, gelatin, albumin, collagen, or dextran.

Another system is a container (e.g., a tube) comprising a subject formulation that is adapted for use with an applicator. An active agent (e.g., a cytosine methylation inhibitor and/or an NF-κB activator) is incorporated into creams, lotions, foams, paste, ointments, and gels which can be applied to the vagina or rectum using an applicator. Processes for preparing pharmaceuticals in cream, lotion, foam, paste, ointment and gel formats can be found throughout the literature. An example of a suitable system is a standard fragrance free lotion formulation containing glycerol, ceramides, mineral oil, petrolatum, parabens, fragrance and water such as the product sold under the trademark JERGENS™ (Andrew Jergens Co., Cincinnati, Ohio). Suitable nontoxic pharmaceutically acceptable systems for use in the compositions of the present invention will be apparent to those skilled in the art of pharmaceutical formulations and examples are described in Remington's Pharmaceutical Sciences, 19th Edition, A. R. Gennaro, ed., 1995. The choice of suitable carriers will depend on the exact nature of the particular vaginal or rectal dosage form desired, e.g., whether the active ingredient(s) is/are to be formulated into a cream, lotion, foam, ointment, paste, solution, or gel, as well as on the identity of the active ingredient(s). Other suitable delivery devices are those described in U.S. Pat. No. 6,476,079.

Subjects Suitable for Treatment

The methods of the present disclosure are suitable for treating individuals who have an immunodeficiency virus infection, e.g., who have been diagnosed as having an immunodeficiency virus infection.

The methods of the present disclosure are suitable for treating individuals who have an HIV infection (e.g., who have been diagnosed as having an HIV infection), and individuals who are at risk of contracting an HIV infection. Such individuals include, but are not limited to, individuals with healthy, intact immune systems, but who are at risk for becoming HIV infected ("at-risk" individuals). At-risk individuals include, but are not limited to, individuals who have a greater likelihood than the general population of becoming HIV infected. Individuals at risk for becoming HIV infected include, but are not limited to, individuals at risk for HIV infection due to sexual activity with HIV-infected individuals. Individuals suitable for treatment include individuals infected with, or at risk of becoming infected with, HIV-1 and/or HIV-2 and/or HIV-3, or any variant thereof.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Celsius, and pressure is at or near atmospheric. Standard abbreviations may be used, e.g., bp, base pair(s); kb, kilobase(s); pl, picoliter(s); s or sec, second(s); min, minute(s); h or hr, hour(s); aa, amino acid(s); kb, kilobase(s); bp, base pair(s); nt, nucleotide(s); i.m., intramuscular(ly); i.p., intraperitoneal (ly); s.c., subcutaneous(ly); and the like.

Example 1

Epigenetic Regulation of HIV-1 Latency

Materials and Methods
Cell Culture and Drug Treatment

Jurkat and J-Lat cells were cultured in RPMI (Invitrogen) with 5% FBS (Gemini Bio-Products) and 5% Fetalplex (Gemini Bio-Products). For analysis of virus reactivation by flow cytometry, aza-CdR (Sigma) and TNF-α (Biosource) treatments were for 24 h, after which medium was replaced. Reactivation was assayed after an additional 48 h. For chromatin immunoprecipitation (ChIP) and bisulfite-mediated methylcytosine mapping, cells were treated for 30 h with aza-CdR. For cycloheximide experiments, cells were treated for 24 hours, either with or without 40 ng/ml cycloheximide.
Plasmid and cDNA Library Generation 20 μg of pEGFP-N1 (Clontech) was methylated at CpGs with M. Sss I (New England Biolabs) according to the manufacturer's protocol. DNA was purified and subjected to a second round of methylation. To generate pBMN-CSI-T, the multiple cloning site (MCS) and green fluorescent protein (GFP) gene from pBMN-1-GFP (Addgene plasmid 1736) were replaced with the MCS from pDNR-LIB (Clontech) and the tomato fluorescent protein. Also, the human cytomegalovirus (hCMV) immediate early promoter was inserted upstream of the MCS. For production of RelA-expressing retrovirus, RelA was cloned from pCMV4(hind), kindly provided by W. Greene, into a version of pBMN-CSI-T lacking the hCMV promoter. MBD2$_{1345-1947}$ was cloned into pBMN-CSI-T as part of cDNA library generation. The cDNA library was generated using the Creator SMART cDNA Library Construction Kit (Clontech) with oligodT-purified (Quickprep mRNA Purification Kit, Amersham) RNA isolated (TRIzol, Invitrogen) from Jurkat T cells. Amplified cDNAs were cloned into pBMN-CSI-T and electroporated into E. coli strain DH5α. The library was amplified 240,000-fold by plating of bacteria on solid medium, and DNA was extracted from aliquots (Plasmid Maxi Kit, Qiagen).
Plasmid Transfection, Cell Infection, and Screening J-Lat cells were transfected by electroporation using Kit R and program O-28 (Amaxa Biosystems). HIV-1 reactivation was assayed by flow cytometry four days post-transfection. HIV-1 R7/E$^-$/GFP pseudotyped with the vesicular stomatitis virus G (VSV-G) protein was produced by cotransfecting 293T cells with pEV1335 and a plasmid encoding VSV-G by the calcium phosphate method. Supernatant was harvested 48 h post-transfection and frozen at −80° C. in aliquots. Aliquots were thawed, diluted 1:160, and used to infect Jurkat T cells overnight at a multiplicity of 0.1 infectious units per cell with 2 ml supernatant per 1 million cells. Three days post-infection, GFP-negative and -positive cell populations were isolated by fluorescence-activated cell sorting (FACS). Retrovirus pseudotyped with VSV-G was produced as described previously [68] by cotransfection of Phoenix-ampho cells with pBMN-CSI-T or plasmids derived thereof and a plasmid encoding VSV-G. Supernatant was harvested 48 h post-transfection and J-Lat cells were infected overnight at a ratio of 250,000 cells to 2 ml supernatant with centrifugation at 2500 rpm for the first 1.5 h. 293T cells were transfected by the calcium phosphate method. Cells were cotransfected with a plasmid encoding the tomato fluorescent protein and either methylated or unmethylated pEGFP-N1, and the tomato-positive population was analyzed for GFP expression. For measurement of J-Lat activation, cells were infected with undiluted virus and analyzed by flow cytometry 2 days post-infection.

For cDNA screening, cells were infected at a multiplicity of 0.15 infectious units per cell. GFP-positive cells were purified by FACS two days post-infection, cultured for two days, and genomic DNA was isolated (DNeasy Tissue Kit, Qiagen). The cDNA inserts were amplified from genomic DNA by polymerase chain reaction (PCR) using oSK57 (5'-AAATGGGCGGTAGGCGTGTACGGTG-3') (SEQ ID NO:4) and oSK58 (5'-GCGGCTTCGGCCAGTAACGT-TAGGG-3') (SEQ ID NO:5) as primers, cloned into pBMN-CSI-T, and identified by determination of nucleotide sequence (Molecular Cloning Laboratories).
Flow Cytometry and FACS Cell fluorescence was measured with the fluorescence activated cell sorter FACSCalibur or LSRII (BD Biosciences). Cell sorting was performed with the fluorescence activated cell sorting (FACS) Vantage DiVa (BD Biosciences). To phenotype CD4$^+$ T cells, the cells were stained with the following monoclonal antibodies (mAbs): phycoerythrin-conjugated (PE)—anti-CD4, TC—anti-CD45RA, or PE—anti-CXCR4 (Caltag). Flow cytometry and sorting data were analyzed with FlowJo software (Treestar) or Cellquest (BD Biosciences), in the case of primary cells. Analysis was restricted to the live population, as defined by the forward versus side scatter profile. Flowjo transforms fluorescence plots to a linear scale at the origin, permitting intelligible display of cells with low fluorescence.

To assess intracellular p24$^{gag}$ expression, cells were fixed and permeabilized with Citofix/Cytoperm (BD Biosciences). Cells were washed with Perm/Wash buffer (BD Biosciences) and were stained with anti-p24 antibody (AG3.0). Cells were washed with Perm/Wash Buffer and incubated with Alexa Fluor 488 goat anti-mouse IgG (H+L) in 100 μl of Perm/Wash buffer. Cells were washed with Perm/Wash buffer and samples were analyzed by flow cytometry. HIV-1 p24$^{gag}$-positive gates were set by comparison with uninfected cells treated in parallel.
Transfection of siRNAs, Reverse Transcription, and Quantitative PCR J-Lat cells were transfected with short interfering RNAs (siRNAs) corresponding to the MBD2 mRNA or non-targeting control short interfering RNAs (siRNAs) (siGENOME SMARTpool or siCONTROL pool, Dharmacon) by electroporation using Kit R and program O-28 (Amaxa Biosystems). Two days after transfection of siRNAs, RNA was isolated from cells with TRIzol Reagent (Invitrogen), treated with DNAse I (Promega), and first strand cDNA was synthesized with reverse transcriptase (Superscript II, Invitrogen) using a dT$_{16}$ primer. Quantitative PCR was performed with the 7900HT Sequence Detection System (Applied Biosystems) and the 2× Hot Sybr real time PCR kit (Molecular Cloning Laboratories), with each PCR reaction receiving 1/20 of the reverse transcription. HIV R7/E⁻/GFP mRNA and DNA were assayed using oSK1 (5'-ATGGTGAGCAAGGGCGAGGAG-3') (SEQ ID NO:6) and oSK5 (5'-GTGGTGCAGATGAACTTCAG-3') (SEQ ID NO:7), oligonucleotides, corresponding to the GFP gene, as primers. HIV R7/E-/GFP DNA was normalized to a DNA sequence upstream of the human β-actin gene using 5USBACT (5'-GCCAGCTGCAAGCCTTGG-3') (SEQ ID NO:8) and 3USBACT [18] (5'-GCCACTGGGCCTCCATTC-3') (SEQ ID NO:9) as primers. MBD2 mRNA was assayed using oSK61 (5'-CCCACAACGAATGAATGAACAGC-3') (SEQ ID NO:10) and oSK62 (5'-TGAAGACCTTTGGGTAGTTCCA-3') (SEQ ID NO:11) as primers. As an internal control, HIV and MBD2 mRNA levels were normalized to that of cyclophilin A. Cyclophilin A mRNA was assayed using oSK6 (5'-GTCTCCTTTGAGCTGTTTGC-3') (SEQ ID NO:12) and oSK7 (5'-CCATAGATGGACTTGCCACC-3') (SEQ ID NO:13) as primers. IκB-α mRNA was assayed using oSK135 (5'-CTCCGAGACTTTCGAGGAAATAC-3') (SEQ ID NO:14) and oSK136 (5'-GCCATTGTAGTTGGTAGCCTTCA-3') (SEQ ID NO:15) as primers. SDS 2.3 software (Applied Biosystems) was used to quantify each cDNA relative to cyclophilin A and to confirm the specificity of each PCR reaction by melting curve analysis.

Bisulfite-Mediated Methylcytosine Mapping

Sodium bisulfite treatment was performed according to the Pikaard protocol (on the internet at http://followed by www(dot)biology(dot)wustl(dot)edu/pikaard/PDFs and protocol files/bisulfite sequencing(dot)pdf) with minor modifications. Jurkat T cell DNA was digested overnight with Pst I and purified with the Qiaquick PCR Purification Kit (Qiagen). Bisulfite-treated DNA was amplified in nested PCR reactions with the following reaction conditions: denature (95° C., 5 minutes), cycle 35 times (95° C., 30 seconds then 60° C., 60 seconds), and extend (60° C., 7 minutes). For J-Lat cells, the first reaction used oSK100 (5'-CGCCTCGAGTTTATTGATTTTTGGATGGTGTTAT-3') (SEQ ID NO:16) and oSK101 (5'-CGCTCTAGACCATTTACCCCTAAATATTCTACAC-3') (SEQ ID NO:17) as primers and the second reaction used oSK71 (5'-CGCCTCGAGATATTTTGTGAGTTTGTATGGGATG-3') (SEQ ID NO:18) and oSK94 (5'-CGCTCTAGACCCAATATTTATCTACAA-3') (SEQ ID NO:19) as primers. For primary cells infected with NL4-3-derived virus, the first reaction used oSK123 (5'-CGCCTCGAGTTTATTGATTTTTGGATGGTGTTTT-3') (SEQ ID NO:20) and oSK124 (5'-CGCTCTAGACCATTTACCCCTAAAAATTCTACAC-3') (SEQ ID NO:21) as primers and the second reaction used oSK122 (5'-CGCCTCGAGATATTTTATGAGTTAGTATGGGATG-3') (SEQ ID NO:22) and oSK94 as primers. All PCR reactions were performed in triplicate and then pooled to reduce chances of clonality in recovered fragments. Products were cleaved with Xho I and Xba I and cloned into pBluescript (Stratagene) cleaved with the same enzymes. Nucleotide sequence was determined of at least nine cloned inserts using the universal M13 reverse primer. The efficiency of sodium bisulfite conversion was calculated using the Quantification Tool for Methylation Analysis (QUMA) software [69]. The nucleotide sequence of untreated DNA was also determined to ensure that readings do not result from virus mutations.

Statistical Analyses

The effect of $MBD2_{1345-1947}$ upon GFP expression (FIG. 2A) was evaluated by a two-tailed, two sample Student's t-test with a null hypothesis of no effect. Reactivation of latent HIV-1 (FIG. 5D) was evaluated with a one-tailed, two sample Student's t-test with a null hypothesis of no increase in GFP expression. In bisulfite-mediated methylcytosine mapping experiments, at least nine independent clones of sodium bisulfite-treated HIV-1 DNA were analyzed from each sample. For J-Lat cell lines in the latent state (FIG. 3B) and CD4⁺ T cells (FIGS. 6D and E), a one-tailed, single sample Student's t-test was performed for each CpG with a null hypothesis of no methylation. For J-Lat 6.3 treated with either aza-CdR or a phosphate buffered saline (PBS) control (FIG. 4A), a one-tailed, two-sample Student's t-test was performed for each CpG with a null hypothesis of no decrease in methylation after 5-aza-2'-deoxycytidine (aza-CdR) treatment. For sorted populations of GFP-negative and -positive Jurkat T cells (FIG. 5B), a one-tailed, two sample Student's t-test was performed for each CpG with the null hypothesis that the GFP-positive population did not have less methylation.

Chromatin Immunoprecipitation and Quantitative PCR

ChIP was performed as described previously [70] with modifications. J-Lat 6.3 cells Cells were diluted to 5×10⁵ per ml, lysed, and sonicated (Model 500 Ultrasonic Dismembranator, Fisher Scientific). Lysates were incubated overnight with 5 μg of antibody against MBD2 (Upstate Cell Signaling Solutions cat. 07-198), HDAC2 (Santa Cruz Biotechnology cat. sc-7899) or Sp1 (Santa Cruz Biotechnology cat. sc-59). Immune complexes were recovered by incubation for 1 h with protein A agarose beads (Invitrogen). Immunoprecipitated DNA was quantified by quantitative PCR using the 7900HT Sequence Detection System (Applied Biosystems) and 2× Hot Sybr real time PCR kit (Molecular Cloning Laboratories). Negative control DNA was assayed using 5USBACT and 3USBACT as primers, CpG island 1 was assayed using oSK92 (5'-TCAGTTCAGATAATTTCAGTTGTCC-3') (SEQ ID NO:23) and oSK93 (5'-CCCAGTACAGGCAAAAAGCA-3') (SEQ ID NO:24) as primers, and CpG island 2 was assayed using oSK89 (5'-AAGCGAAAGGGAAACCAGAG-3') (SEQ ID NO:25) and oSK90 (5'-TCTCCCCCGCTTAATACTGA-3') (SEQ ID NO:26) as primers. SDS 2.3 software (Applied Biosystems) was used to analyze precipitated DNA relative to input and to confirm the specificity of each PCR reaction by melting curve analysis.

Differentiation, Infection, and Activation of CD4⁺ T Cells Ex Vivo

Peripheral blood mononuclear cells (PBMCs) were obtained from leukopaks from unidentified, healthy donors. Naïve CD4⁺ T cells were isolated by magnetic activated cell separation (MACS) microbead negative sorting using the naïve T cell isolation kit (Miltenyi Biotec). The purity of the population was always higher than 95%. Naïve T cells were primed with beads coated with anti-CD3 and anti-CD28 (Dynal/Invitrogen) as previously described [44].

Seven days after stimulation, cells were infected by spinoculation. Seven days after infection, cells were reactivated with beads coated with anti-CD3 and anti-CD28 for 72 h in the presence of IL-2 at a ratio of 1 bead per cell. The integrase inhibitor 118-D-24 did not have any effect on viral reactivation.

Results

A Genetic Screen to Identify Novel Regulators of HIV-1 Latency

The J-Lat cells are clonal cell lines isolated after infection of Jurkat cells with a HIV-1 virus encoding green fluorescent protein (GFP). Latently infected cells were selected that were GFP-negative at the basal state but became GFP-positive after treatment with tumor necrosis factor-alpha (TNF-α). Treatment of each cell line with TNF-α reactivated latent HIV-1 to a different extent, depending on the cell line (FIG. 1A). To identify cellular genes that control HIV-1 latency in this system, a complementary DNA (cDNA) library was made from the Jurkat T cell line and cloned into a plasmid encoding the pBMN-CSI-T retrovirus vector, which expresses tomato fluorescent protein as a marker (FIG. 1B).

To confirm that this vector mediates expression of cloned cDNAs at a level sufficient for reactivation of latent HIV-1, a positive control virus was produced that encodes NF-κB RelA, which reactivates latent HIV-1 in J-Lat cells [18]. Infection of J-Lat cell line 6.3 with the RelA-encoding virus caused a 3.5-fold increase in HIV-1 gene expression compared to a control virus that lacks an insert (FIG. 1C).

The cDNA library was packaged into retroviral particles and introduced into the J-Lat 6.3 cell line via infection (Table 1). GFP-positive cells, indicative of reactivated latent HIV-1, were isolated by fluorescence activated cell sorting (FACS). cDNA library inserts were amplified from genomic DNA obtained from these cells by PCR with virus-specific primers and recloned into pBMN-CSI-T.

TABLE 1 cDNA screening

| | |
|---|---|
| Library complexity | 1,000,000 independent clones |
| Cells analyzed | 15,000,000 |
| Cells receiving cDNA insert (live gate)[a] | 2,100,000 (14%) |
| Cells with reactivated HIV-1 (live gate)[b] | 58,235 |
| Cells with cDNA insert and reactivated HIV-1[c] | 11,122 (19%) |
| cDNA clones[d] | 11,122 |

[a]Tomato-positive cells in live gate. Percentage is consistent with single-hit infection kinetics.
[b]GFP-positive cells in live gate.
[c]Tomato-positive cells in the GFP-positive gate. Greater number of tomato-positive cells than in live gate, indicating that GFP selection enriches for cDNAs that reactivate latent HIV-1.
[d]Clones that potentially reactivate latent HIV-1.

FIGS. 1A-C. A cDNA screen to identify novel regulators of HIV-1 latency. (A) Flow cytometry of latent HIV-1 reactivation in indicated J-Lat cell lines after treatment with PBS or TNF-α. GFP-positive cells are indicated by gate and percentage. (B) Genome of retrovirus vector used in expression screen. (C) Flow cytometry of latent HIV-1 reactivation in J-Lat 6.3 cells after transduction with retrovirus expression vectors marked with the tomato fluorescent protein. Histograms indicate GFP expression after gating for tomato fluorescent protein-positive cells.

MBD2 Regulates HIV-1 Latency and Repression of Methylated DNA

One clone identified in this screen, $MBD2_{1345-1947}$, corresponded to nucleotides 1345-1947 of the mRNA encoding the MBD2 transcriptional repressor. Importantly, the first ATG within this clone is in frame with the authentic MBD2 initiation codon, indicating a truncated protein corresponding to amino acids 388 to 411 of full-length MBD2 could be translated.

MBD2 is a member of the methyl-CpG binding domain family of proteins, which possess methyl-CpG binding domains (MBDs). Similar to other members of this family, MBD2 specifically binds methylated DNA and mediates transcriptional repression by recruitment of the nucleosome remodeling and histone deacetylation (NuRD) complex that includes chromatin remodeling and HDAC activities [35-37].

Figure 2:
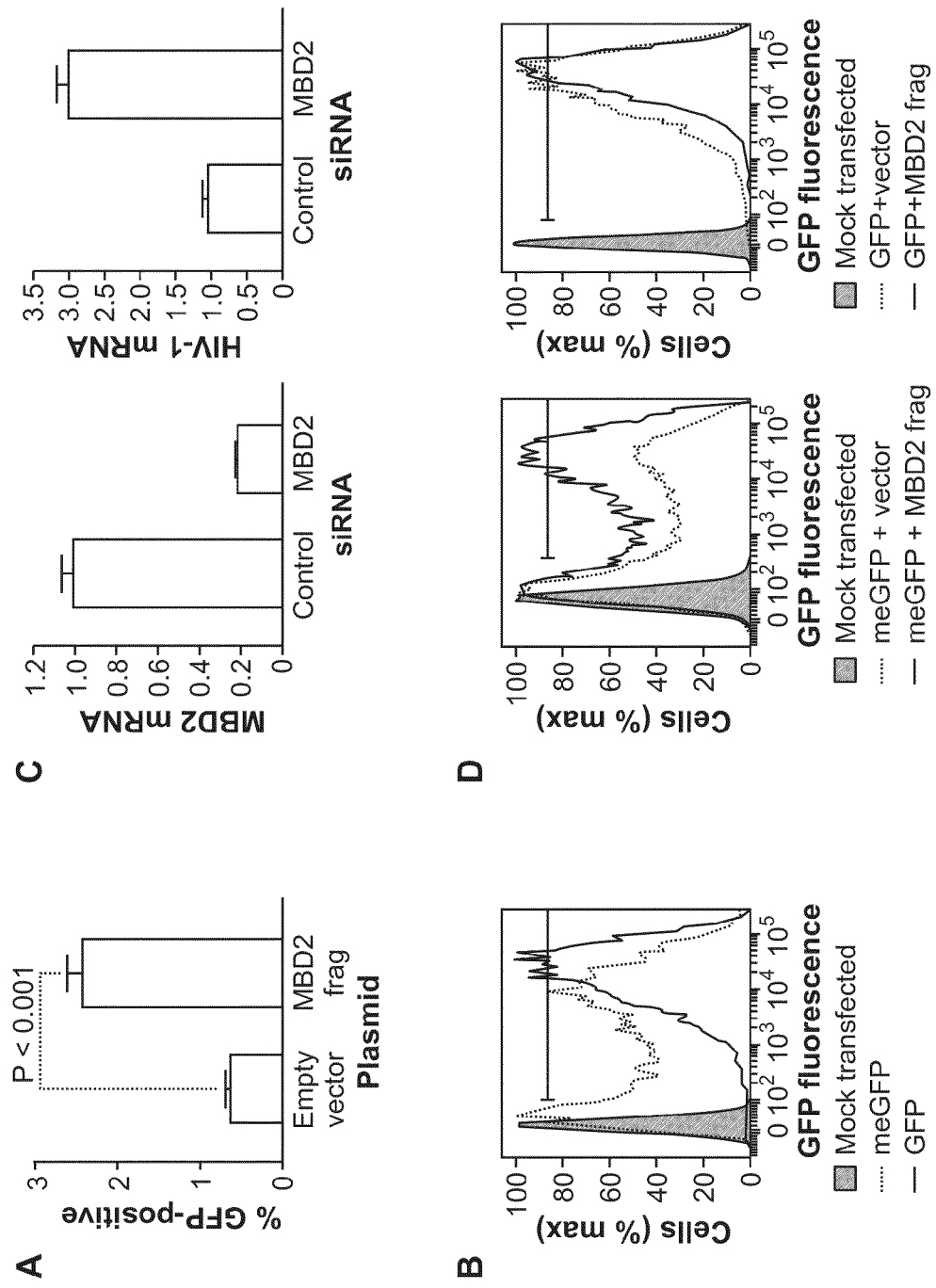
FIGS. 2A-D depict MBD2 regulation of HIV-1 latency.

To confirm that $MBD2_{1345-1947}$ reactivates latent HIV-1, J-Lat cells were transfected with an expression vector for this polypeptide. Transfection of J-Lat 6.3 with $MBD2_{1345-1947}$ induced a 5-fold greater reactivation of latent HIV-1 in comparison to an empty vector control (FIG. 2A). Since MBD2 inhibits transcription of methylated DNA [35], the identification of a C-terminal fragment of MBD2 in our screen indicated that this fragment inhibits endogenous MBD2 function in a dominant-negative manner. Furthermore, identification of this fragment implicated full-length, endogenous MBD2 in the repression of HIV-1 transcription during latency. To establish the role of endogenous MBD2 in HIV-1 latency, J-Lat 6.3 was transfected with a pool of siRNAs corresponding to this factor. This resulted in an 80 percent reduction in the level of MBD2 mRNA compared to cells transfected with a non-targeting control siRNA pool (FIG. 2B, left panel). Depletion of MBD2 resulted in a 300 percent increase in HIV-1 mRNA compared to those transfected with the control siRNA pool (FIG. 2B, right panel). These data demonstrate that MBD2 participates in the repression of HIV-1 transcription during latency.

Since MBD2 inhibits transcription of methylated DNA [35], we believed the C-terminal MBD2 fragment identified in our screen might reactivate latent virus by inhibiting endogenous MBD2 function. To test $MBD2_{1345-1947}$ for this activity, we examined its effect on transcription of methylated DNA in a heterologous system. 293T cells were cotransfected with an expression vector for $MBD2_{1345-1947}$ and with another plasmid encoding GFP under the control of the CMV promoter (pEGFP-N1). This latter plasmid was either methylated in vitro (meGFP) or left unmethylated (GFP). Plasmid methylation was confirmed by resistance to Hpa II cleavage and reduced GFP expression in transfected 293T cells (FIG. 2C). Importantly, cotransfection of the $MBD2_{1345-1947}$ plasmid with methylated pEGFP-N1 increased the proportion of GFP-positive cells from 58 to 72 percent (FIG. 2D, left panel). Furthermore, derepression by $MBD2_{1345-1947}$ was preferential for methylated DNA, and a similar effect was not observed with non-methylated pEGFP-N1 (FIG. 2D, right panel). These results implicate MBD2 and cytosine methylation in the regulation of HIV-1 latency in the J-Lat system.

FIGS. 2A-D. MBD2 regulates HIV-1 latency and transcriptional repression. (A) Latent HIV-1 reactivation in J-Lat 6.3 cells after transfection with the indicated expression plasmids and flow cytometry. Percent GFP-positive cells after gating for tomato-positive cells is shown. Experiment was performed in triplicate and error bars represent standard deviation. (B) Transcriptional activation of latent HIV-1 in J-Lat 6.3 after transfection with a siRNA that targets MBD2. Levels of MBD2 (left panel) or HIV-1 (right panel) mRNA were determined by reverse transcription and quantitative PCR and normalized to those after transfection with a non-targeting control siRNA. Data are representative of three different experiments. Error bars indicate standard deviation of qPCR results. (C) Flow cytometry of GFP expression in 293T cells that were mock transfected, transfected with methylated pEGFP-N1 (meGFP), or with unmethylated pEGFP-N1 (GFP). Gate indicates GFP-positive cells. (D) Flow cytometry of GFP expression in 293T cells cotransfected with methylated pEGFP-N1 (left panel) or unmethylated pEGFP-N1 (right panel) and an expression vector marked by the tomato fluorescent protein. Tomato-positive cells were gated to measure GFP expression in populations that received a control vector lacking an insert or one that encodes $MBD2_{1345-1947}$. Gates indicate GFP-positive cells.

HIV-1 Latency is Associated with Cytosine Methylation in Provirus CpG Islands

Figure 3:
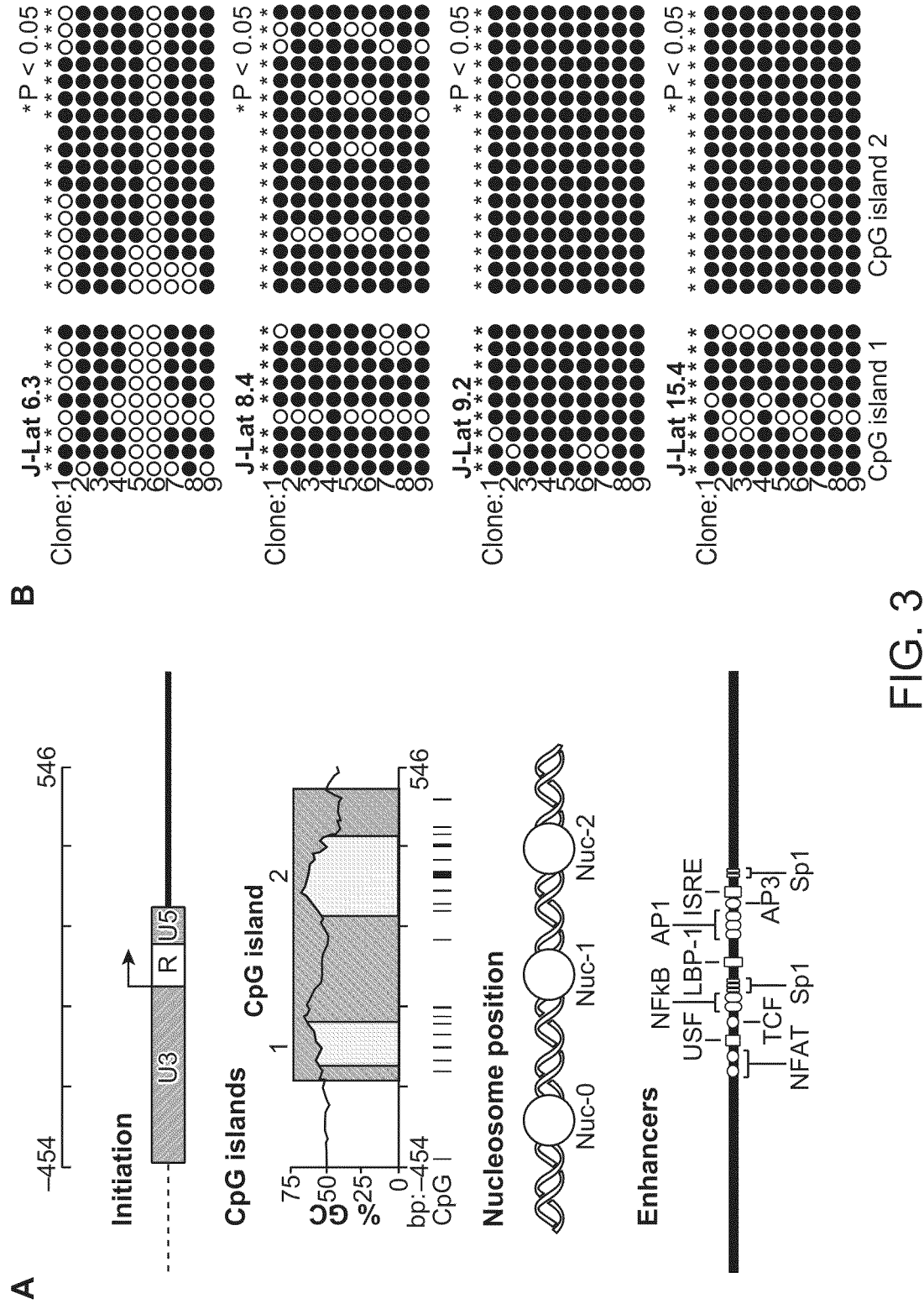
FIGS. 3A and 3B depict CpG islands in HIV-1 that are methylated during latency.

Cytosine methylation is an epigenetic modification that inhibits transcription when CpG islands, clusters of CpG dinucleotides proximal to a transcription start site, are hypermethylated [38]. To determine whether the HIV-1 genome encodes CpG islands, the methprimer program [39] was used search the HIV-1 provirus nucleotide sequence. Two CpG islands were identified flanking the transcription start site at positions −194 to −94 and 180 to 368 (FIG. 3A). These islands overlap with two regions that were previously shown to be nucleosome-free [40] and rich in transcription factor binding sites [41], two features usually associated with bona fide CpG islands [38]. To determine whether HIV-1 CpG islands are methylated during latency, their methylation state was analyzed by bisulfite-mediated methylcyto sine mapping. FIG. 7 shows the nucleotide sequence of the HIV-1 promoter, positions of CpG islands, and the particular CpGs subjected to methylation analysis. We found that both CpG islands were hypermethylated in four different J-Lat cell lines, with the majority of CpGs methylated more than 70 percent of the time (FIG. 3B). In sodium bisulfite-treated DNA, cytosine was converted to thymine in greater than 99 percent of all CpN dinucleotides (N=A, T, or C), confirming efficient bisulfite conversion of non-methylated cytosines.

FIGS. 3A and 3B. HIV-1 encodes two CpG islands that are methylated during latency. (A) Attributes of DNA surrounding HIV-1 transcript initiation site. Initiation: Transcription initiation site within HIV-1 LTR is indicated by arrow. CpG islands: Plot of GC content of DNA surrounding initiation site. Light grey areas indicate CpG islands 1 and 2. Vertical lines indicate CpGs. Nucleosome position: Locations of nucleosomes in HIV-1 promoter. Enhancers: Transcription factor binding sites. (B) Bisulfite-mediated methylcytosine mapping of latent HIV-1 in J-Lat cells. CpG islands 1 and 2 and J-Lat line are indicated. Each column represents one CpG position, with each circle in the column indicating either cytosine (open circles) or methylcytosine (filled circles) in an independently cloned DNA molecule. Asterisks indicate cytosines with statistically significant methylation.

Cytosine Methylation Recruits Transcriptional Repressors to the HIV-1 Promoter

Figure 4:
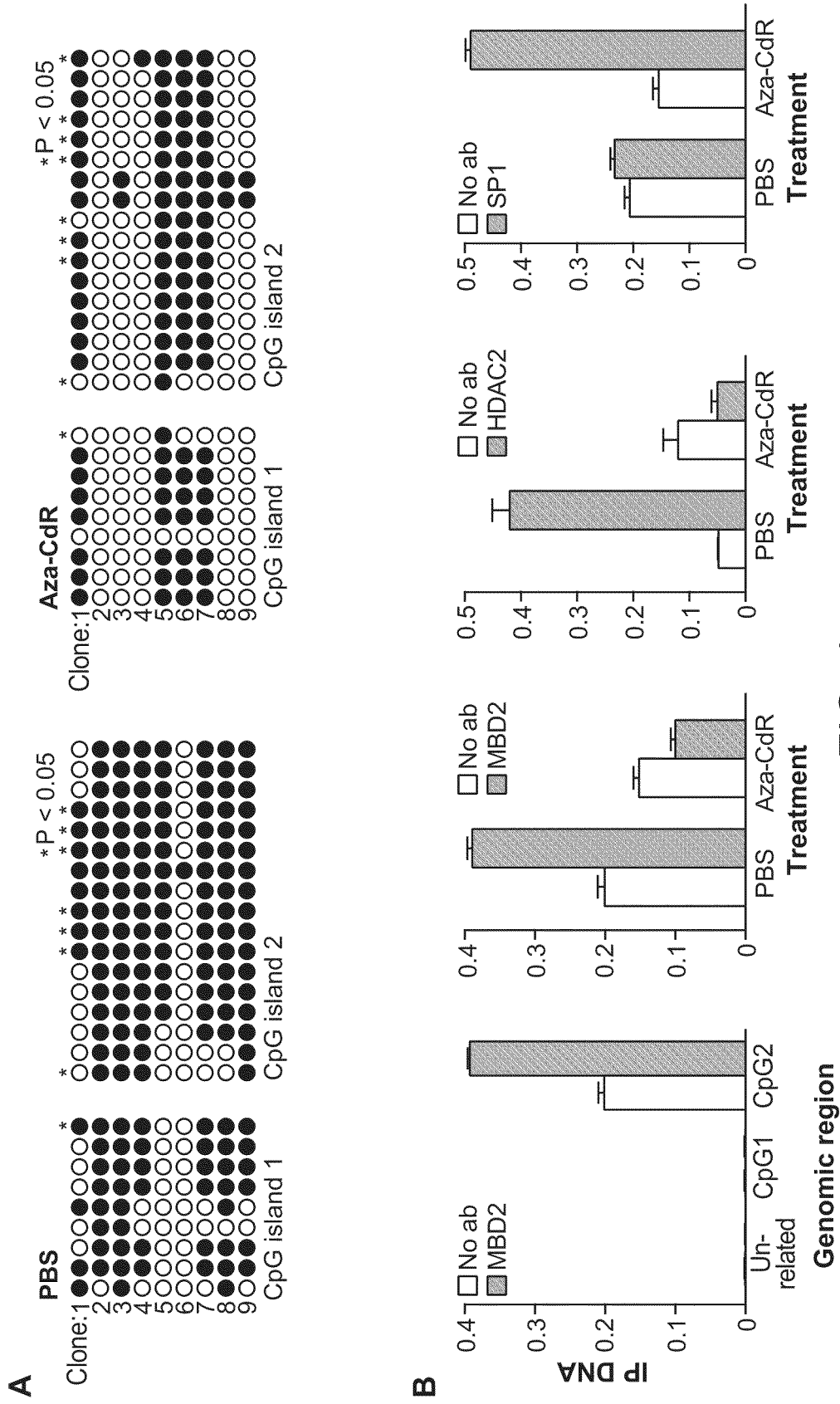
FIGS. 4A-F depict methylation-dependent recruitment of transcription factors and maintenance of HIV-1 latency.

MBD2 mediates transcriptional repression by acting as a bridge between hypermethylated CpG islands and chromatin modifying enzymes, including HDACs [42]. To test whether MBD2 is recruited to the HIV-1 provirus in vivo, we performed chromatin immunoprecipitation (ChIP) assays. Chromatin from J-lat cells was incubated with MBD2 antisera and the immunoprecipitated material analyzed by quantitative PCR for presence of HIV-1 provirus. We observed recruitment of MBD2 to CpG island 2 of the HIV-1 genome, but observed no recruitment to CpG island 1 in comparison to a negative control (FIG. 4B, first panel). Treatment of J-Lat 6.3 with aza-CdR, an inhibitor of DNA methylation, caused up to a 50 percent decrease in methylation, depending on the CpG analyzed (FIG. 4A), demonstrating that HIV-1 DNA methylation is reversible. It should be noted that the data for PBS-treated J-Lat 6.3 in FIGS. 3B and 4A are from the same experiment. Importantly, MBD2 recruitment to CpG island 2 was eliminated when cytosine methylation was inhibited by treatment of the cells with aza-CdR (FIG. 4B, second panel). Next, we tested for the presence of HDAC2, an MBD2 cofactor, at CpG island 2 during latency. Comparable to MBD2, HDAC2 was recruited to CpG island 2 during latency and was lost after treatment with aza-CdR (FIG. 4B, third panel). In contrast, inhibition of methylation by aza-CdR was associated with increased Sp1 recruitment to CpG island 2 (FIG. 4B, fourth panel). These data demonstrate that during latency, multiple components of the NuRD complex recognize the methylated HIV-1 CpG island 2 and that this recruitment may be pharmacologically reversed.

Synergistic Reactivation of Latent HIV-1 by aza-CdR and NF-κB Activators

The finding that methylation of CpG islands flanking the HIV-1 transcription start site can be reversed with aza-CdR suggests that aza-CdR could reactivate latent HIV-1. Aza-CdR alone, however, showed little effect in terms of mean fluorescence intensity or the proportion of GFP-positive cells (FIGS. 4C and 4D). As previously observed, treatment with TNF-α reactivated latent HIV-1 in only a fraction of the cell population ranging from 16 to 41 percent depending on the J-Lat cell line studied (FIG. 1A). In contrast, dual treatment of latently infected J-Lat clonal cell lines (lines 6.3, 8.4, 9.2 and 15.4) with both aza-CdR and TNF-α induced a dramatic increase in HIV-1 gene expression (FIGS. 4C and 4D). Powerful synergy was observed when aza-CdR was used at concentrations as low as 0.5 µM in combination with TNF-α or the NF-κB activator prostratin (FIG. 4E). The combination of aza-CdR and TNF-α increased HIV-1 expression 196-, 101-, 76-, and 47-fold over PBS-treated control cells (FIG. 4D, upper panel and Table 2). Each of these increases was nearly 20-fold greater than the additive effect of the two reagents (Table 2).

TABLE 2

Reactivation of latent HIV-1

| | MFI, fold greater than PBS control | | | |
|---|---|---|---|---|
| J-Lat cell line | Aza-CdR | TNF-a | Aza-CdR + TNF-a | Fold greater than additive effect[a] |
| 6.3 | 1.8 | 7.1 | 196.4 | 21.9 |
| 8.4 | 1.6 | 2.5 | 101.9 | 24.7 |
| 9.2 | 1.1 | 2.3 | 76.1 | 22.5 |
| 15.4 | 1 | 1.7 | 47.1 | 17.7 |

[a]The magnitude of HIV-1 reactivation after treatment with both Aza-CdR and TNF-α was divided by the summed individual magnitudes after Aza-CdR or TNF-α treatment.

Synergistic activation of transcription was specific for the HIV-1 promoter. Analysis of J-Lat 6.3 by RT-PCR found that aza-CdR and TNF-α synergistically activated HIV-1 transcription but had only an additive effect on transcription of IκB-α, another NF-κB-regulated gene. The same result was observed for J-Lat 8.4. Aza-CdR and TNF-α synergistically activated HIV-1 transcription but had only an additive effect on transcription of IκB-α. To determine if aza-CdR acts directly on HIV-1 transcription, J-Lat cells were treated with cycloheximide to inhibit expression of other factors. Cycloheximide activity was confirmed by the inhibition of GFP expression after treatment of J-Lat cells with TNF-α. Under these conditions, aza-CdR still induced HIV-1 transcription, indicating that aza-CdR acts directly upon the HIV-1 provirus. Synergistic reactivation of latent virus was not observed when aza-CdR was combined with the HDAC inhibitor valproic acid (VPA). Weak synergistic reactivation was observed when aza-CdR was combined with the HDAC inhibitor suberoylanilide hydroxamic acid (SAHA), with an effect about two-fold greater than the additive effect of the drugs.

We show in four different J-Lat cell lines that near-complete reactivation of latent HIV-1 required treatment with both an NF-κB activator and an inhibitor of DNA methylation (FIG. 4D, lower panel). J-Lat A2 is another clone that harbors a latent HIV-derived vector encoding only the viral promoter and Tat. In contrast to the other cell lines analyzed here, latent virus in J-Lat A2 did not require aza-CdR for full reactivation. TNF-α alone reactivated the majority of latent virus in J-Lat A2 (FIGS. 4D, lower panel, and 4F) [33]. These data show that treatment with a methylation inhibitor is necessary for full reactivation of some, but not all, J-Lat cell lines.

FIGS. 4A-F. Methylation-dependent recruitment of transcription factors and maintenance of HIV-1 latency. (A) Bisulfite-mediated methylcytosine mapping of HIV-1 in J-Lat 6.3 cells treated with PBS (left panel) or aza-CdR (right panel). Asterisks indicate cytosines with a statistically significant lesser level of methylation in cells treated with aza-CdR. (B) Panel 1: Chromatin immunoprecipitation analysis of MBD2 recruitment to an unrelated DNA sequence between the β-actin and fascin-1 genes (unrelated), HIV-1 CpG island 1 (CpG1), and HIV-1 CpG island 2 (CpG2). Panels 2-4: Chromatin immunoprecipitation analysis of MBD2, HDAC2, or Sp1 recruitment to CpG island 2 in cells treated with PBS or aza-CdR. Data are representative of three independent experiments. Error bars indicate standard deviation of quantitative PCR results. (C) Flow cytometric analysis of latent HIV-1 reactivation in the indicated J-Lat clones after treatment with aza-CdR, TNF-α, or aza-CdR plus TNF-α. Histograms indicate GFP fluorescence. Gates indicate GFP-positive cells. (D) Bar graph representation of reactivation data. HIV-1 expression was normalized to control cells treated with PBS, and either GFP fluorescence (top panel) or percentage of GFP-positive cells (bottom panel) is displayed. Results are representative of three independent experiments. (E) Latent HIV-1 reactivation in J-Lat 6.3 treated with increasing doses of aza-CdR alone, in combination with TNF-α, or in combination with prostratin. Data points on the y-axis represent fluorescence at 0 μM Aza-CdR. GFP fluorescence was measured by flow cytometry and normalized to control cells treated with PBS. Error bars indicate standard deviation of three experiments. (F) Latent HIV-1 reactivation in the J-Lat cell line A2 treated with aza-CdR, TNF-α, or aza-CdR plus TNF-α. Gate indicates GFP-positive cells.

Figure 5:
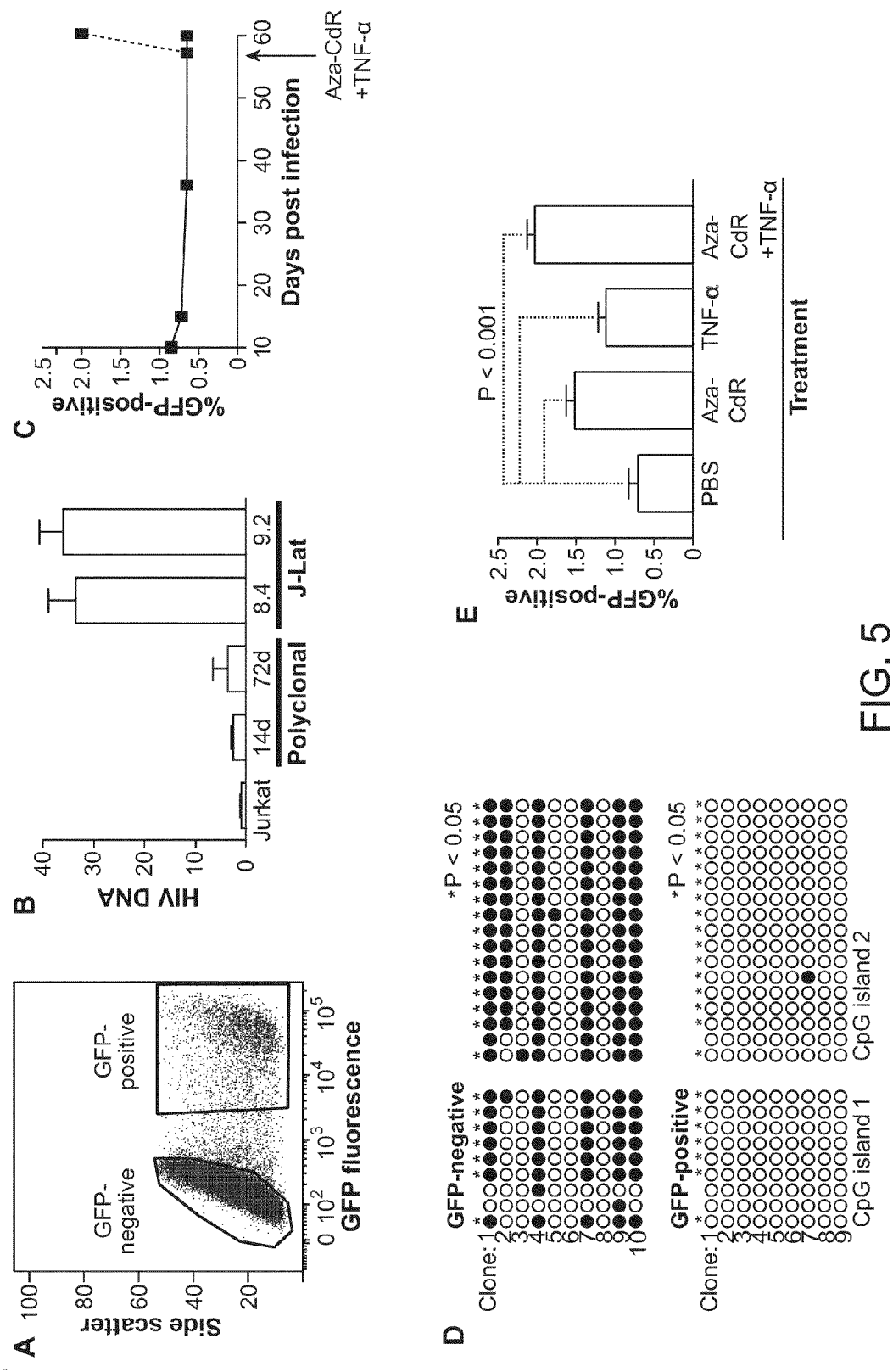
FIGS. 5A-E depict the effect of cytosine methylation on HIV-1 latency in polyclonal Jurkat T cells.

Cytosine Methylation Contributes to HIV-1 Latency in a Polyclonal Cell Population To confirm that cytosine methylation is regularly associated with HIV-1 latency, a polyclonal population of latently infected Jurkat T cells was generated by infection with virus produced from the R7/E−/GFP clone. All HIV-1 proteins are expressed from this full length HIV-1 molecular clone, except Nef, which is replaced with GFP, and Env, which is suppressed by a frameshift mutation. FACS was used to separate latently infected/uninfected GFP-negative cells from productively infected GFP-positive cells (FIG. 5A). To compare the infection rate of this population to that of the J-Lat cells, quantitative PCR for HIV R7/E-/GFP sequence was performed on genomic DNA from the polyclonal population 14 and 72 days post infection. The quantity of HIV-1 DNA was normalized to cellular DNA using PCR primers that anneal upstream of the β-actin gene. The level of HIV DNA in these cells ranged from 9- to 14-fold less than that detected in J-Lat cells, indicating a lower rate of infection (FIG. 5B). Bisulfite-mediated methylcytosine mapping of HIV-1 DNA from the productive population found hypomethylation, with no detectable methylation at most CpGs. In direct contrast, methylcytosine mapping of the latent population found hypermethylation, with the majority of CpGs methylated more than 68 percent of the time (FIG. 5D). In sodium bisulfite-treated DNA, cytosine was converted to thymine in greater than 99 percent of all CpN dinucleotides (N=A, T, or C), confirming efficient bisulfite conversion of non-methylated cytosines.

Reactivation of latent HIV-1 was also examined in this population. After approximately two months, the proportion of cells with active HIV-1 remained stable at 0.65% (FIG. 5C). Cells were then treated with TNF-α, aza-CdR, or TNF-α plus aza-CdR. TNF-α reactivated latent HIV-1, with a 1.5-fold greater proportion of cells with active virus (FIG. 5E). Importantly, latent HIV-1 was also reactivated by aza-CdR alone, with a two-fold greater proportion of cells with active virus (FIG. 5D). These observations indicate that, after infection of Jurkat cells in vitro, a subset of latently infected cells exists that can be reactivated solely by inhibition of DNA methylation.

FIGS. 5A-E. Cytosine methylation maintains HIV-1 latency in polyclonal Jurkat T cells. (A) Flow cytometry of Jurkat T cells infected with HIV-1 R7/E−/GFP clone. Gates indicate GFP-positive (productively infected) and GFP-negative (latently infected and uninfected) cells. (B) Quantitative PCR to measure HIV-1 DNA in infected Jurkat cells. For polyclonal cell populations, days after infection are indicated. For J-Lat clones, cell line is indicated. Levels of HIV-1 DNA were normalized to cellular DNA. Y-axis indicates fold over uninfected Jurkat negative control. Experiment was performed in triplicate and error bars indicate standard deviation. (C) HIV-1 expression over time in a polyclonal population of latently infected and uninfected Jurkat T cells. GFP fluorescence was measured by flow cytometry. The time point at which cells were treated with aza-CdR plus TNF-α is indicated on the x-axis. (D) Bisulfite-mediated methylcytosine mapping of HIV-1 CpG islands in polyclonal Jurkat T cells that are latently infected (GFP-negative, upper panel) or productively infected (GFP-positive, lower panel). Asterisks indicate cytosines with a statistically significant greater level of methylation in the GFP-negative population. (E) Latent HIV-1 reactivation in a polyclonal population of latently infected and uninfected Jurkat T cells treated with aza-CdR, TNF-α, or aza-CdR plus TNF-α. HIV-1 expression was measured by flow cytometry for GFP, and the percentage of cells that express GFP is displayed. Error bars indicate standard deviation of three experiments.

HIV-1 Latency is Associated with Cytosine Methylation in Primary Cells

The similarities of J-Lat cells to latently infected $CD4^+$ T cells have established the utility of this experimental system for identifying and characterizing mechanisms of HIV-1 latency. However, because J-Lat cells divide autonomously and possess other aberrations associated with cellular transformation, cytosine methylation was analyzed in a recently developed primary cell model of latency [43]. In this system, naïve $CD4^+$ T cells are purified from uninfected donors and activated under conditions that drive them to become memory cells with either a Th1, Th2, or non-polarized (NP) phenotype [44]. These differentiated cells are then infected with HIV-1 and viral expression is monitored. The phenotype of NP cells generated ex vivo closely resembles that of central memory $CD4^+$ T cells found in vivo, which persist for years in secondary lymphoid organs and can differentiate into effector memory $CD4^+$ T cells [45]. A high rate of HIV-1 latency is observed in NP memory $CD4^+$ T cells [43].

Figure 6:
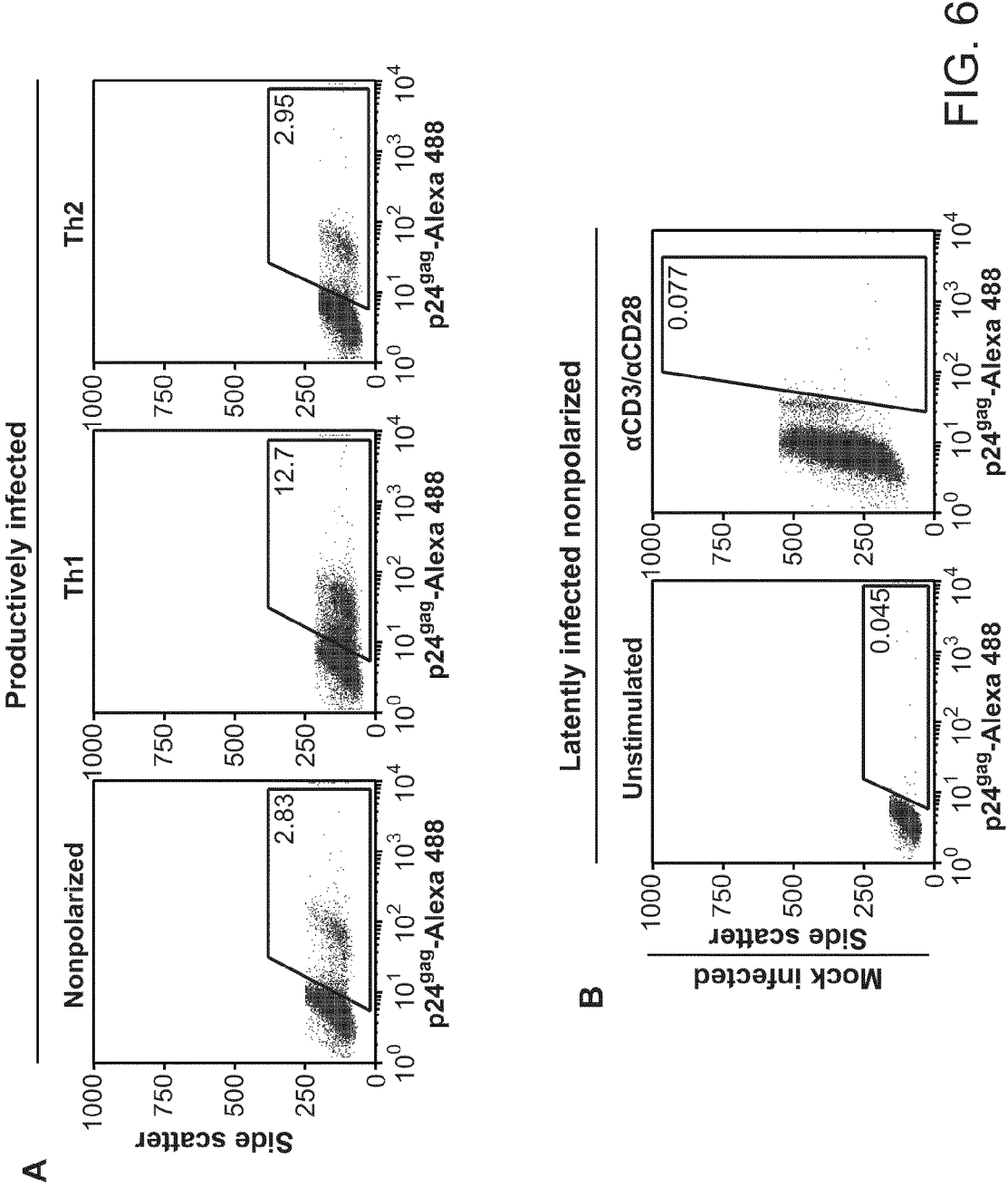
FIGS. 6A-E depict association of cytosine methylation with HIV-1 latency in primary $CD4^+$ T cells.
Figure 6:
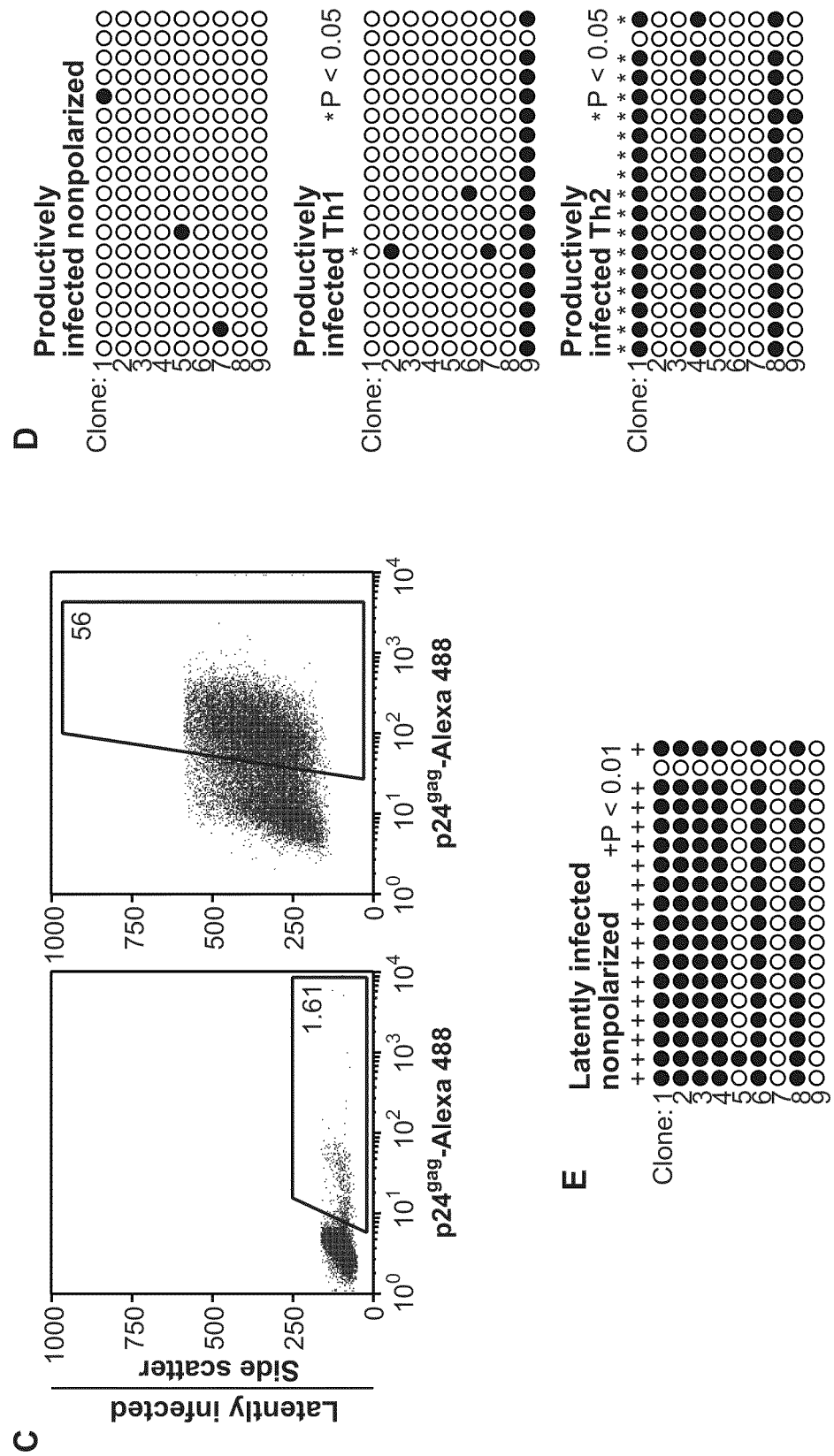

To determine if HIV-1 latency is associated with cytosine methylation in primary $CD4^+$ T cells, bisulfite-mediated methylcytosine mapping was performed on $CD4^+$ T cells activated under NP, Th1, and Th2 polarizing conditions and infected with HIV-1. Cells were infected with virus produced from the DHIV virus clone [46], in which CpG island 2 is conserved. Five days post-infection, p24$^{gag}$ was detected in all three subsets (FIG. 6A). At this early time point, the HIV-1 CpG island in the NP and Th1 populations was hypomethylated, with most CpGs methylated only 0 or 10 percent of the time, respectively (FIG. 6D). Significant methylation was detected in Th2 cells, with most CpGs methylated 33 percent of the time (FIG. 6D). Two weeks post-infection, NP cells had returned to a quiescent state and HIV-1 gene expression, as measured by intracellular p24$^{gag}$ expression, was low (FIG. 6C, left panel). However, stimulation with antibodies against CD3 and CD28 dramatically increased HIV-1 gene expression, indicating a large population of latently infected cells (FIG. 6C, right panel). Importantly, CpG island methylation in latently infected NP cells was greater than in productively infected NP cells, with the majority of CpGs methylated 67 percent of the time (FIG. 6E). In sodium bisulfite-treated DNA, cytosine was converted to thymine in greater than 98 percent of all CpN dinucleotides (N=A, T, or C), confirming efficient bisulfite conversion of non-methylated cytosines. These data confirm that T cell quiescence is associated with methylation of HIV-1 CpG islands and latency in memory CD4$^+$ T cells.

FIGS. 6A-E. Cytosine methylation is associated with HIV-1 latency in primary CD4+ T cells. (A) Flow cytometric analysis of HIV-1 gene expression in CD4$^+$ T cells productively infected under non-polarizing, Th1, or Th2 conditions. HIV-1 was detected by intracellular staining for p24$^{gag}$. Gates indicate gag-positive cells, and the percentage of positive cells is indicated. (B,C) Flow cytometric analysis of HIV-1 gene expression in (B) mock infected or (C) latently infected CD4$^+$ T cells under non-polarizing conditions, either at the basal state or after reactivation with antibodies against CD3 and CD28. HIV-1 was detected by intracellular staining for p24$^{gag}$. Gates indicate gag-positive cells, and the percentage of gag-positive cells is indicated. (D) Bisulfite-mediated methylcytosine mapping of HIV-1 CpG island 2 in actively infected CD4$^+$ T cells infected under non-polarizing, Th1, or Th2 conditions. (E) Bisulfite-mediated methylcytosine mapping of HIV-1 CpG island 2 in latently infected CD4$^+$ T cells stimulated under non-polarizing conditions.

1. Gulick R M, Mellors J W, Havlir D, Eron J J, Gonzalez C, et al. (1997) Treatment with indinavir, zidovudine, and lamivudine in adults with human immunodeficiency virus infection and prior antiretroviral therapy. N Engl J Med 337: 734-739.
2. Hammer S M, Squires K E, Hughes M D, Grimes J M, Demeter L M, et al. (1997) A controlled trial of two nucleoside analogues plus indinavir in persons with human immunodeficiency virus infection and CD4 cell counts of 200 per cubic millimeter or less. AIDS Clinical Trials Group 320 Study Team. N Engl J Med 337: 725-733.
3. Perelson A S, Essunger P, Cao Y, Vesanen M, Hurley A, et al. (1997) Decay characteristics of HIV-1-infected compartments during combination therapy. Nature 387: 188-191.
4. Palella F J, Jr., Delaney K M, Moorman A C, Loveless M O, Fuhrer J, et al. (1998) Declining morbidity and mortality among patients with advanced human immunodeficiency virus infection. HIV Outpatient Study Investigators. N Engl J Med 338: 853-860.
5. Chun T W, Carruth L, Finzi D, Shen X, DiGiuseppe J A, et al. (1997) Quantification of latent tissue reservoirs and total body viral load in HIV-1 infection. Nature 387: 183-188.
6. Chun T W, Stuyver L, Mizell S B, Ehler L A, Mican J A, et al. (1997) Presence of an inducible HIV-1 latent reservoir during highly active antiretroviral therapy. Proc Natl Acad Sci USA 94: 13193-13197.
7. Finzi D, Hermankova M, Pierson T, Carruth L M, Buck C, et al. (1997) Identification of a reservoir for HIV-1 in patients on highly active antiretroviral therapy. Science 278: 1295-1300.
8. Wong J K, Hezareh M, Gunthard H F, Havlir D V, Ignacio C C, et al. (1997) Recovery of replication-competent HIV despite prolonged suppression of plasma viremia. Science 278: 1291-1295.
9. Chun T W, Davey R T, Jr., Engel D, Lane H C, Fauci A S (1999) Re-emergence of HIV after stopping therapy. Nature 401: 874-875.
10. Chun T W, Davey R T, Jr., Ostrowski M, Shawn Justement J, Engel D, et al. (2000) Relationship between pre-existing viral reservoirs and the re-emergence of plasma viremia after discontinuation of highly active anti-retroviral therapy. Nat Med 6: 757-761.
11. Zhang L, Chung C, Hu B S, He T, Guo Y, et al. (2000) Genetic characterization of rebounding HIV-1 after cessation of highly active antiretroviral therapy. J Clin Invest 106: 839-845.
12. Forsdyke D R (1991) Programmed activation of T-lymphocytes. A theoretical basis for short term treatment of AIDS with azidothymidine. Medical Hypotheses 34: 24.
13. Geeraert L, Kraus G, Pomerantz R J (2008) Hide-and-seek: the challenge of viral persistence in HIV-1 infection. Annu Rev Med 59: 487-501.
14. Pierson T, McArthur J, Siliciano R F (2000) Reservoirs for HIV-1: mechanisms for viral persistence in the presence of antiviral immune responses and antiretroviral therapy. Annu Rev Immunol 18: 665-708.
15. Coull J J, Romerio F, Sun J M, Volker J L, Galvin K M, et al. (2000) The human factors YY1 and LSF repress the human immunodeficiency virus type 1 long terminal repeat via recruitment of histone deacetylase 1. J Virol 74: 6790-6799.
16. du Chene I, Basyuk E, Lin Y L, Triboulet R, Knezevich A, et al. (2007) Suv39H1 and HP1gamma are responsible for chromatin-mediated HIV-1 transcriptional silencing and post-integration latency. Embo J 26: 424-435.
17. Marban C, Redel L, Suzanne S, Van Lint C, Lecestre D, et al. (2005) COUP-TF interacting protein 2 represses the initial phase of HIV-1 gene transcription in human microglial cells. Nucleic Acids Res 33: 2318-2331.
18. Williams S A, Chen L F, Kwon H, Ruiz-Jarabo C M, Verdin E, et al. (2006) NF-kappaB p50 promotes HIV latency through HDAC recruitment and repression of transcriptional initiation. Embo J 25: 139-149.
19. Tyagi M, Karn J (2007) CBF-1 promotes transcriptional silencing during the establishment of HIV-1 latency. Embo J 26: 4985-4995.
20. Lassen K, Han Y, Zhou Y, Siliciano J, Siliciano R F (2004) The multifactorial nature of HIV-1 latency. Trends Mol Med 10: 525-531.
21. Han Y, Lassen K, Monie D, Sedaghat A R, Shimoji S, et al. (2004) Resting CD4+ T cells from human immunodeficiency virus type 1 (HIV-1)-infected individuals carry integrated HIV-1 genomes within actively transcribed host genes. J Virol 78: 6122-6133.

22. Lewinski M K, Bisgrove D, Shinn P, Chen H, Hoffmann C, et al. (2005) Genome-wide analysis of chromosomal features repressing human immunodeficiency virus transcription. J Virol 79: 6610-6619.
23. Lenasi T, Contreras X, Peterlin B M (2008) Transcriptional interference antagonizes proviral gene expression to promote HIV latency. Cell Host Microbe 4: 123-133.
24. Han Y, Lin Y B, An W, Xu J, Yang H C, et al. (2008) Orientation-dependent regulation of integrated HIV-1 expression by host gene transcriptional readthrough. Cell Host Microbe 4: 134-146.
25. Jordan A, Defechereux P, Verdin E (2001) The site of HIV-1 integration in the human genome determines basal transcriptional activity and response to Tat transactivation. Embo J 20: 1726-1738.
26. Lassen K G, Ramyar K X, Bailey J R, Zhou Y, Siliciano R F (2006) Nuclear retention of multiply spliced HIV-1 RNA in resting CD4+ T cells. PLoS Pathog 2: e68.
27. Huang J, Wang F, Argyris E, Chen K, Liang Z, et al. (2007) Cellular microRNAs contribute to HIV-1 latency in resting primary CD4+ T lymphocytes. Nat Med 13: 1241-1247.
28. Stellbrink H J, van Lunzen J, Westby M, O'Sullivan E, Schneider C, et al. (2002) Effects of interleukin-2 plus highly active antiretroviral therapy on HIV-1 replication and proviral DNA (COSMIC trial). Aids 16: 1479-1487.
29. Prins J M, Jurriaans S, van Praag R M, Blaak H, van Rij R, et al. (1999) Immuno-activation with anti-CD3 and recombinant human IL-2 in HIV-1-infected patients on potent antiretroviral therapy. Aids 13: 2405-2410.
30. van Praag R M, Prins J M, Roos M T, Schellekens P T, Ten Berge I J, et al. (2001) OKT3 and IL-2 treatment for purging of the latent HIV-1 reservoir in vivo results in selective long-lasting CD4+ T cell depletion. J Clin Immunol 21: 218-226.
31. Siliciano J D, Lai J, Callender M, Pitt E, Zhang H, et al. (2007) Stability of the Latent Reservoir for HIV-1 in Patients Receiving Valproic Acid. The Journal of Infectious Diseases 195: 833.
32. Steel A, Clark S, Teo I, Shaunak S, Nelson M, et al. (2006) No change to HIV-1 latency with valproate therapy. Aids 20: 1681-1682.
33. Jordan A, Bisgrove D, Verdin E (2003) HIV reproducibly establishes a latent infection after acute infection of T cells in vitro. Embo J 22: 1868-1877.
34. Fenaux P (2005) Inhibitors of DNA methylation: beyond myelodysplastic syndromes. Nat Clin Pract Oncol 2 Suppl 1: S36-44.
35. Wade P A (2001) Methyl CpG-binding proteins and transcriptional repression. Bioessays 23: 1131-1137.
36. Bird A P, Wolffe A P (1999) Methylation-Induced Repression—Belts, Braces, and Chromatin. Cell 99: 451.
37. Zhang Y, Ng H H, Erdjument-Bromage H, Tempst P, Bird A, et al. (1999) Analysis of the NuRD subunits reveals a histone deacetylase core complex and a connection with DNA methylation. Genes Dev 13: 1924-1935.
38. Antequera F (2003) Structure, function and evolution of CpG island promoters. Cell Mol Life Sci 60: 1647-1658.
39. Li L C, Dahiya R (2002) MethPrimer: designing primers for methylation PCRs. Bioinformatics 18: 1427-1431.
40. Verdin E, Paras P, Jr., Van Lint C (1993) Chromatin disruption in the promoter of human immunodeficiency virus type 1 during transcriptional activation. Embo J 12: 3249-3259.
41. el Kharroubi A, Verdin E (1994) Protein-DNA interactions within DNase I-hypersensitive sites located downstream of the HIV-1 promoter. Journal of Biological Chemistry 269: 19916-19924.
42. Lopez-Sena L, Esteller M (2008) Proteins that bind methylated DNA and human cancer: reading the wrong words. Br J Cancer 98: 1881-1885.
43. Bosque A, Planelles V (2008) Induction of HIV-1 latency and reactivation in primary memory CD4+ T cells Blood: First Edition Paper, prepublished online Oct. 10, 2008.
44. Messi M, Giacchetto I, Nagata K, Lanzavecchia A, Natoli G, et al. (2003) Memory and flexibility of cytokine gene expression as separable properties of human T(H)1 and T(H)$_2$ lymphocytes. Nat Immunol 4: 78-86.
45. Sallusto F, Lenig D, Forster R, Lipp M, Lanzavecchia A (1999) Two subsets of memory T lymphocytes with distinct homing potentials and effector functions. Nature 401: 708-712.
46. Andersen J L, DeHart J L, Zimmerman E S, Ardon O, Kim B, et al. (2006) HIV-1 Vpr-induced apoptosis is cell cycle dependent and requires Bax but not ANT. PLoS Pathog 2: e127.
47. Brooks D G, Arlen P A, Gao L, Kitchen C M, Zack J A (2003) Identification of T cell-signaling pathways that stimulate latent HIV in primary cells. Proc Natl Acad Sci USA 100: 12955-12960.
48. Folks T M, Clouse K A, Justement J, Rabson A, Duh E, et al. (1989) Tumor necrosis factor alpha induces expression of human immunodeficiency virus in a chronically infected T-cell clone. Proc Natl Acad Sci USA 86: 2365-2368.
49. West M J, Lowe A D, Karn J (2001) Activation of Human Immunodeficiency Virus Transcription in T Cells Revisited: NF-{kappa}B p65 Stimulates Transcriptional Elongation. The Journal of Virology 75: 8524.
50. Williams S A, Chen L F, Kwon H, Fenard D, Bisgrove D, et al. (2004) Prostratin antagonizes HIV latency by activating NF-kappaB. J Biol Chem 279: 42008-42017.
51. Kim Y K, Bourgeois C F, Pearson R, Tyagi M, West M J, et al. (2006) Recruitment of TFIIH to the HIV LTR is a rate-limiting step in the emergence of HIV from latency. Embo J 25: 3596-3604.
52. Williams S A, Kwon H, Chen L F, Greene W C (2007) Sustained induction of NF-kappa B is required for efficient expression of latent human immunodeficiency virus type 1. J Virol 81: 6043-6056.
53. Marban C, Suzanne S, Dequiedt F, de Walque S, Redel L, et al. (2007) Recruitment of chromatin-modifying enzymes by CTIP2 promotes HIV-1 transcriptional silencing. Embo J 26: 412-423.
54. Ooi S K, Bestor T H (2008) Cytosine methylation: remaining faithful. Curr Biol 18: R174-176.
55. Weber M, Hellmann I, Stadler M B, Ramos L, Paabo S, et al. (2007) Distribution, silencing potential and evolutionary impact of promoter DNA methylation in the human genome. Nat Genet. 39: 457-466.
56. Vaissiere T, Sawan C, Herceg Z (2008) Epigenetic interplay between histone modifications and DNA methylation in gene silencing. Mutation Research/Reviews in Mutation Research In Press, Corrected Proof.
57. Rountree M R, Bachman K E, Herman J G, Baylin S B (2001) DNA methylation, chromatin inheritance, and cancer. Oncogene 20: 3156-3165.
58. Weber M, Davies J J, Wittig D, Oakeley E J, Haase M, et al. (2005) Chromosome-wide and promoter-specific analyses identify sites of differential DNA methylation in normal and transformed human cells. Nat Genet. 37: 853-862.

59. Ishida T, Hamano A, Koiwa T, Watanabe T (2006) 5' long terminal repeat (LTR)-selective methylation of latently infected HIV-1 provirus that is demethylated by reactivation signals. Retrovirology 3: 69.
60. Jeening a R E, Westerhout E M, van Gerven M L, Berkhout B (2008) HIV-1 latency in actively dividing human T cell lines. Retrovirology 5: 37.
61. Obrien M C, Ueno T, Jahan N, Zajackaye M, Mitsuya H (1995) HIV-1 Expression Induced by Anticancer Agents in Latently HIV-1-Infected ACH$_2$ Cells. Biochemical and Biophysical Research Communications 207: 903.
62. Pion M, Jordan A, Biancotto A, Dequiedt F, Gondois-Rey F, et al. (2003) Transcriptional suppression of in vitro-integrated human immunodeficiency virus type 1 does not correlate with proviral DNA methylation. J Virol 77: 4025-4032.
63. Saunthararajah Y, Hillery C A, Lavelle D, Molokie R, Dorn L, et al. (2003) Effects of 5-aza-2'-deoxycytidine on fetal hemoglobin levels, red cell adhesion, and hematopoietic differentiation in patients with sickle cell disease. Blood 102: 3865-3870.
64. Mund C, Hackanson B, Stresemann C, Lubbert M, Lyko F (2005) Characterization of DNA Demethylation Effects Induced by 5-Aza-2'-Deoxycytidine in Patients with Myelodysplastic Syndrome. Cancer Research 65: 7086-7090.
65. Christman J K (2002) 5-Azacytidine and 5-aza-2'-deoxycytidine as inhibitors of DNA methylation: mechanistic studies and their implications for cancer therapy. Oncogene 21: 5483-5495.
66. Ghoshal K, Datta J, Majumder S, Bai S, Kutay H, et al. (2005) 5-Aza-deoxycytidine induces selective degradation of DNA methyltransferase 1 by a proteasomal pathway that requires the KEN box, bromo-adjacent homology domain, and nuclear localization signal. Mol Cell Biol 25: 4727-4741.
67. Korin Y D, Brooks D G, Brown S, Korotzer A, Zack J A (2002) Effects of prostratin on T-cell activation and human immunodeficiency virus latency. J Virol 76: 8118-8123.
68. Pear W S, Nolan G P, Scott M L, Baltimore D (1993) Production of high-titer helper-free retroviruses by transient transfection. Proc Natl Acad Sci USA 90: 8392-8396.
69. Kumaki Y, Oda M, Okano M (2008) QUMA: quantification tool for methylation analysis. Nucleic Acids Research 36: W170-175.
70. Yu J, Angelin-Duclos C, Greenwood J, Liao J, Calame K (2000) Transcriptional repression by blimp-1 (PRDI-BF1) involves recruitment of histone deacetylase. Mol Cell Biol 20: 2592-2603.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

What is claimed is:

1. A method of reactivating latent immunodeficiency virus in an immunodeficiency virus-infected cell, the method comprising contacting the cell with a synergistically effective amount of an inhibitor of cytosine methylation and an NF-κB activator, wherein the cytosine methylation inhibitor is 5-aza-2'deoxycytidine, and wherein the NF-κB activator is TNF-α or prostratin, wherein the inhibitor of cytosine methylation and the NF-κB activator synergistically reactivate the latent immunodeficiency virus.

2. A method of reducing the number of cells containing a latent human immunodeficiency virus in an individual, the method comprising:
    administering to the individual a synergistically effective amount of an inhibitor of cytosine methylation and an NF-κB activator, wherein the cytosine methylation inhibitor is 5-aza-2' deoxycytidine, and wherein the NF-κB activator is TNF-α or prostratin.

3. The method of claim 2, wherein said administering is effective to reduce the number of cells containing a latent human immunodeficiency virus in the individual by at least 20%.

4. The method of claim 1, wherein the cytosine methylation inhibitor is 5-aza-2'deoxycytidine and wherein the NF-κB activator is TNF-α.

5. The method of claim 1, wherein the cytosine methylation inhibitor is 5-aza-2'deoxycytidine and wherein the NF-κB activator is prostratin.

6. The method of claim 2, wherein the cytosine methylation inhibitor is 5-aza-2'deoxycytidine and wherein the NF-κB activator is TNF-α.

7. The method of claim 2, wherein the cytosine methylation inhibitor is 5-aza-2'deoxycytidine and wherein the NF-κB activator is prostratin.

* * * * *